US00RE35281E

United States Patent [19]

Inukai et al.

[11] E Patent Number: Re. 35,281

[45] Reissued Date of Patent: Jun. 18, 1996

[54] TETRAZOLE DERIVATIVES AND ALDOSE REDUCTASE INHIBITION THEREWITH

[75] Inventors: Sinji Inukai, Hatano; Mitsuzi Agata, Oi-machi; Kiyoshi Akiba, Yamakita-machi; Takeo Ohmura, Oi-machi; Yoshihiro Horio, Hatano; Yasuhiro Ootake, Minami-ashigara; Shohei Sawaki, Hodaka-machi; Masayoshi Goto, Tokyo, all of Japan

[73] Assignee: Wakamoto Pharmaceutical Co., Ltd., Tokyo, Japan

[21] Appl. No.: 178,666

[22] Filed: Jan. 7, 1994

Related U.S. Patent Documents

Reissue of:

[64] Patent No.: 5,055,481
Issued: Oct. 8, 1991
Appl. No.: 497,500
Filed: Mar. 22, 1990

[30] Foreign Application Priority Data

Mar. 24, 1989 [JP] Japan ..... 1-70520

[51] Int. Cl.[6] ..... C07D 257/04; A61K 31/41

[52] U.S. Cl. ..... 548/253

[58] Field of Search ..... 514/381; 548/253

[56] References Cited

PUBLICATIONS

Sorensen et al, *Acta Chem. Scand.* 26:541–548, 1972.
Buckler et al, *J. Med. Chem.* 13:725–729, 1970.

*Primary Examiner*—David B. Springer
*Attorney, Agent, or Firm*—Seed and Berry

[57] ABSTRACT

The present invention relates to an aldose reductase inhibitor having the following formula:

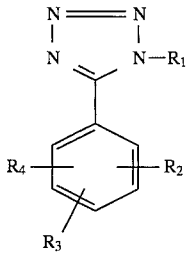

$R_1$ is a hydrogen atom or —A—$COOR_5$ (A is an alkylene group having 1 to 4 carbon atoms and $R_5$ is a hydrogen atom or a lower alkyl group), and $R_2$, $R_3$ and $R_4$ are the same as or different from each other and selected from the group consisting of a hydrogen atom, a hydroxy group, a halogen atom, a carboxyl group, an alkyl group, an amide group, an amino group, an alkoxy group, an aryl group, an aryloxy group, an alkylthio group, an alkylsulfinyl group, an alkylsulfonyl group, a nitro group, —$NHCOCOOR_6$ ($R_6$ is a hydrogen atom or a lower alkyl group), a mono- or dialkylaminosulfonyl group, and a residual group having the following formula:

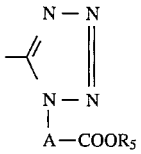

(A and $R_5$ are the same as in the above).

The compounds defined in the above are excellent in aldose reductase inhibitory activity and low in toxicity. Therefore, those compounds are useful as a preventive agent and/or a remedy for diabetic complications such as neuropathy, retinopathy, nephropathy, cataracts and keratopathy.

10 Claims, No Drawings

TETRAZOLE DERIVATIVES AND ALDOSE REDUCTASE INHIBITION THEREWITH

Matter enclosed in heavy brackets [ ] appears in the original patent but forms no part of this reissue specification; matter printed in italics indicates the additions made by reissue.

FIELD OF THE INVENTION

The present invention relates to an aldose reductase inhibitor. Namely, the present invention relates to an aldose reductase inhibitor containing the following compound as an effective component.

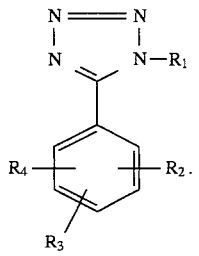

[I]

$R_1$ is a hydrogen atom or —A—$COOR_5$ (A is an alkylene group having 1 to 4 carbon atoms and $R_5$ is a hydrogent atom or a lower alkyl group), and $R_2$, $R_3$ and $R_4$ are the same as or different from each other and selected from the group consisting of a hydrogen atom, a hydroxy group, a halogen atom, a carboxyl group, an alkyl group, an amide group, an amino group, an alkoxy group, an aryl group, an aryloxy group, an alkylthio group, an alkylsulfinyl an alkylsulfonyl group, a nitro group, —$NHCOCOOR_6$ ($R_6$ is a hydrogen atom or a lower alkyl group), a mono- or dialkylaminosulfonyl group, and a residual group having the following formula:

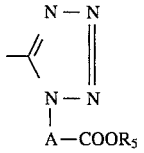

(A and $R_5$ are the same as in the above).

BACKGROUND OF THE INVENTION

An aldose reductase inhibitor is useful as a preventive agent and/or a remedy for diabetic complications. The diabetic complications appear in various forms, such as neuropathy, retinopathy, nephropathy, cataracts and keratopathy. It has been known that these diseases are triggered by hyperglycemia and caused by abnormal increase of the production of sorbitol in the polyol pathway to abnormally accumulate a large amount of sorbitol in the cells.

The present aldose reductase inhibitor remarkably and effectively inhibits the activity of aldose reductase. which catalyzes the production of sorbitol in the polyol pathway, to prevent the production of sorbitol. As a result, the present aldose reductase inhibitor acts as a useful preventive agent/remedy for diabetic complications.

Dr. Tsuyoshi Tanimoto [Division of Biological Chemistry and Reference Standards, National Institute of Hygienic Sciences] reported that aldose reductase inhibitors are effective for prevention/treatment of diabetic complications [FARUMASHIA, 24, No. 5, p. 459~463 (1988)]. This article discloses the chemical structures and $IC_{50}$ (concentrations for inhibiting activities by 50%) of representative aldose reductase inhibitors such as Alrestatin, Tolrestat, 4-Isopropyl-BPOC, Sorbinil, M-79175, Alconil, AND-138, Epalrestat, CT- 112 and Statil.

The effective compounds having the formula [I] comprise both known and novel.

For example, the compounds listed in Table 1 are described, as an antiallergic agent.

TABLE 1

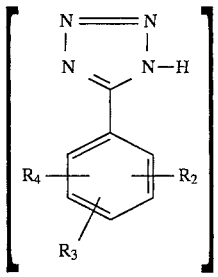

| Publication | $R_2$ | $R_3$ | $R_4$ |
|---|---|---|---|
| (A) | —NHCOCOO-alkyl (2-position) | H | H |
| (B) | —NHCOCOO-alkyl | H. lower alkyl. lower alkoxy or halogen | H. lower alkyl. lower alkoxy or halogen |
| (C) | —NHCOCOO-alkyl (3-position) | H or halogen | —NHCOCOO-alkyl (5-position) |

TABLE 1-continued

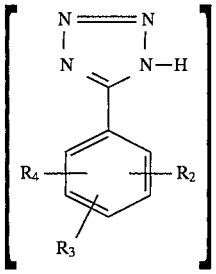

| Publication | $R_2$ | $R_3$ | $R_4$ |
|---|---|---|---|
| (D) | —NHCOCOOH (3-position) | H | H |

Note:
(A) Japanese Patent Publication for Opposition Purpose (J.P. Kokoku) No. 59-1704
(B) J. P. Kokoku No. 59-1705
(C) J. P. Kokoku No. 59-1707
(D) Japanese Patent Unexamined Published Application (J. P. Kokai) No. 63-44570

The compounds listed in Table 2 are described in J. Org. Chem., 21, 311 (1956).

TABLE 2

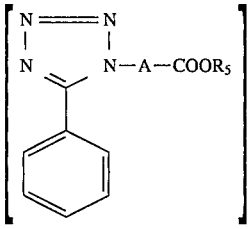

| A | $R_5$ |
|---|---|
| $-CH_2-$ | H |
| $-CH(CH_3)-$ | H |
| $-C(CH_3)_2-$ | H |
| $-C(CH_3)_2-$ | $C_2H_5$ |

The compounds listed in Table 3 are also described in Zh. Org. Khim., 18, 1981 (1982).

TABLE 3

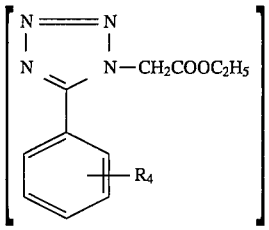

| $R_4$ | | | |
|---|---|---|---|
| 3-$CH_3$. | 3-Cl. | 3-$NO_2$. | |
| 4-$CH_3$. | 4-Cl. | 4-Br. | 4-$NO_2$ |

However, it has not been known until now that the present compounds have a useful inhibitory activity for aldose reductase.

SUMMARY OF THE INVENTION

The object of the present invention is to provide an aldose reductase inhibitor which has an excellent inhibitory effect to aldose reductase and which is very effective as a preventive agent and/or a remedy for diabetic complications with low toxicity to human body.

In the course of intensively studying the aminophenyl tetrazole derivatives in Table 1, which have been found to be useful as an antiallergic agent (J.P. Kokoku Nos. 59–1704, 59–1705 and 59–1707 and J.P. Kokai No. 63–44570), in respect of other pharmacological activities than the antiallergic activity, the present inventors have found out that those compounds have a very useful inhibitory activity for aldose reductase.

In order to develop much excellent compounds, the present inventors have synthesized many compounds similar to the known compounds above and made intensive studies on those compounds including screening. As a result, the present inventors have found out that the novel compounds having the general formula [I] are very excellent aldose reductase inhibitors. The present invention has been completed based on this finding.

Namely, the present invention relates to an aldose reductase inhibitor containing, as an effective component, a compound having the following general formula [I]:

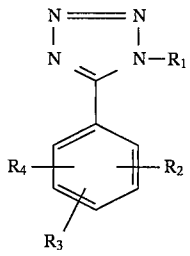

[I]

$R_1$ is a hydrogen atom or —A—$COOR_5$ (A is an alkylene group having 1 to 4 carbon atoms and $R_5$ is a hydrogen atom or a lower alkyl group), and $R_2$, $R_3$ and $R_4$ are the same as or different from each other and selected from the group consisting of a hydrogen atom, a hydroxy group, a halogen atom, a carboxyl group, an alkyl group, an amide group, an amino group, an alkoxy group, an aryl group, an aryloxy group, an alkylthio group, an alkylsulfinyl group, an alkylsulfonyl group, a nitro group, —$NHCOCOOR_6$ ($R_6$ is a hydrogen atom or a lower alkyl group), a mono- or dialkylaminosulfonyl group, and a residual group having the following formula:

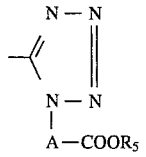

(A and $R_5$ are the same as in the above).

DETAILED EXPLANATION OF THE INVENTION

In the above formula, the alkylene group as A is preferably those having 1 to 4 carbon atoms. The group A may have a substituent such as an alkyl group like a methyl group.

The lower alkyl group as $R_5$ is preferably those having 1 to 6 carbon atoms, more preferably 1 to 2 carbon atoms, such as a methyl group and an ethyl group.

The alkyl group as $R_2$, $R_3$ or $R_4$ is preferably those having 1 to 10 carbon atoms, more preferably 1 to 7 carbon atoms.

The amido group as $R_2$, $R_3$ or $R_4$ is generally those amido groups derived from monoalkyl amino compounds. dialkyl amino compounds, or cyclic amino compounds. Such monoalkyl amino compounds include those amine compounds having an alkyl group of $C_1$ to $C_7$. Such dialkyl amino compounds include those compounds having an alkyl group of $C_1$ to $C_7$. Such cyclic amino compounds include those compounds such as piperidine.

The alkyl group of the alkoxy group, alkylthio group, alkyl sulfinyl group, alkylsulfonyl group or mono- or dialkylaminosulfonyl group is preferably those having 1 to 7 carbon atoms.

The phenyl or phenoxy group as $R_2$, $R_3$ or $R_4$ may have a substituent.

The dosage per day of the present compound is dependent on the degree of the symptom of a patient. In general, it is 1 to 1000 mg per adult. The dosage is usually administered at one time or at several times.

The administration can be made in any form. For example, it can be made orally, subcutaneously, intravenously, muscularly, or locally.

The present compound is usually used in various forms, such as a tablet, a powder, a fine particle, a granule, a capsule, a ball, a solution, an injection, an eye drop, and the like, using additives, which are conventionally used, such as a diluent including sodium citrate, calcium carbonate, calcium phosphate and lactic acid, a disintegrator including corn starch and alginic acid, a binder including gelatin and acacia gum, and a lubricant including magnesium stearate, sodium lauryl sulfate and talc.

The present compound can be synthesized as follows. In this case, the definitions of A and $R_1$~$R_6$ are the same as the above, Hal means a halogen atom, and Ar means

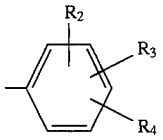

-continued

Reaction I
(hydrogen atom as $R_1$ is changed to $-A-COOR_5$)

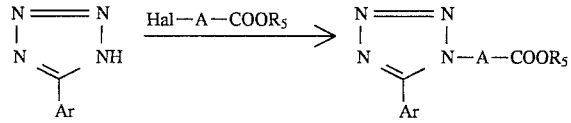

Reaction 2
(synthesis of tetrazole ring)

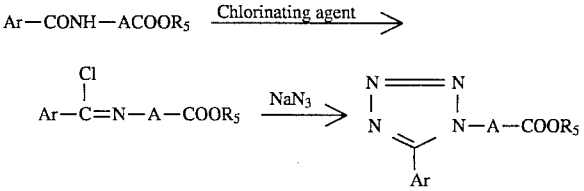

Reaction 3
($R_5$ is changed to a hydrogen atom)

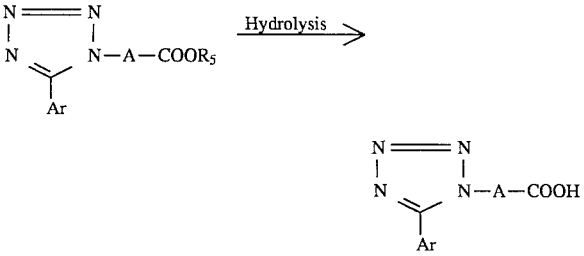

Reaction 4
(synthesis of the compound wherein $R_2$ is $-NHCOCOOR_6$)

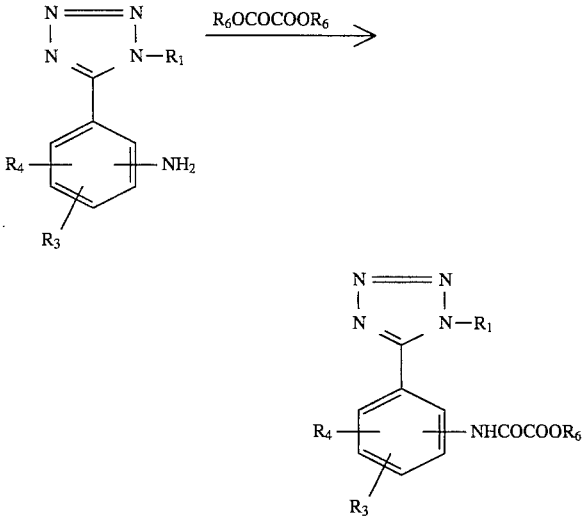

Reaction 5
($R_6$ is changed to a hydrogen atom)

-continued

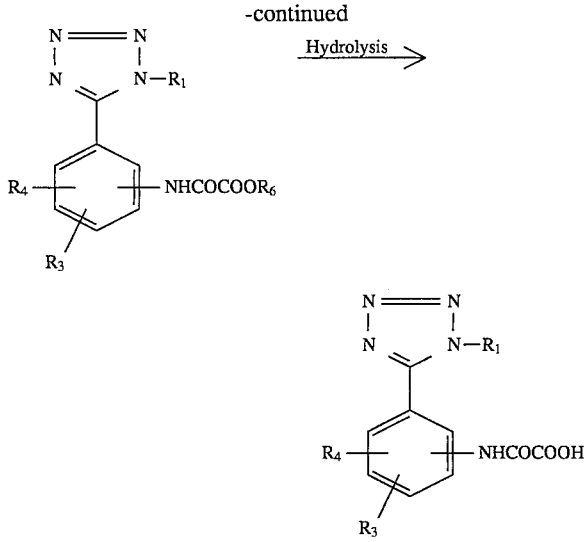

In Reaction 1, the reaction is preferably conducted in a solvent such as methanol, ethanol or propanol, below the boiling point of the solvent.

Reaction 2 corresponds to a tetrazole cyclization reaction. In this reaction, N-aryloylaminoalkyl carboxylate is reacted with a chlorinating agent such as phosphorus pentachloride or thionyl chloride, to produce an imidoylchloride, which is then reacted with sodium azide to give the object compound. The synthetic reaction of the imidoyl chloride can be conducted in a solvent such as benzene or toluene. The reaction temperature is preferably room temperature or lower.

In the cyclization reaction, the intermediate imidoylchloride can be used without purifying it. Sodium azide is preferably used in an amount 1.5 to 3 times (in mole) that of the imidoylchloride. The reaction is preferably conducted in dimethylformamide at room temperature.

Reaction 3 shows that if the compound wherein $R_5$ is a hydrogen atom is necessary to be produced, the carboxylate produced in Reaction 1 or 2 is merely hydrolyzed. This hydrolysis reaction can be conducted in the presence of a base such as sodium hydroxide or potassium hydroxide, or an acid such as hydrochloric acid. sulfuric acid, acetic acid or trifluoroacetic acid.

Reaction 4 shows a representative process for synthesizing the compound having the formula [I] wherein $R_2$ is —$NHCOCOOR_6$ and indicates the reaction between an aminophenyl tetrazole having an amino group as a position where $R_2$ is introduced and an alkyl oxalate.

This reaction can be conducted in an inert organic solvent which has been used for organic synthetic reactions. It is preferable that the reaction should be conducted using, as a solvent, a greatly excessive amount of the feed reactant, the alkyl oxalate (generally, 5 to 10 times (in mole) that of the other reactant). The reaction temperature is preferably 100° to 180° C.

Reaction 5 shows that the compound obtained by Reaction 4 can be hydrolyzed at an ester position, if the compound wherein $R_6$ is a hydrogen atom is necessary to be obtained.

The resultant compound having the formula [I] can be isolated and purified through the conventional chemical processes such as extraction, recrystallization or column chromatography. The purified compound is used as an effective component of an aldose reductase inhibitor.

EXAMPLE

The present invention will be explained in detail below in reference to the following examples.

EXAMPLE 1 (REACTION 1)

(1-1) Methyl 5-phenyl-l-tetrazoleacetate

Two grams of 5-phenyltetrazole (13.68 mM) were slowly added to 5 ml of a methanol solution containing 770 mg (13.68 mM) of potassium hydroxide at room temperature. Two milli liters of a methanol solution containing 1.48 g (13.68 mM)of methyl chloroacetate were dropwise added to the resultant solution at room temperature. After the completion of the addition, the reaction solution was refluxed for 20 hours and cooled. The reaction solution was diluted with ethyl acetate and washed with water. The organic phase was dried over anhydrous magnesium sulfate and evaporated under reduced pressure. The residue was purified by silica gel chromatography (elute is chloroform), to give 0.54 g of methyl 5-phenyl-1-tetrazoleacetate (yield: 18.1%).

N.M.R.($CDCl_3$) δ: 3.81(s,3H), 5.21(s,2H), 7.35–7.67(m, 5H).

I.R. $_{\nu Na\ Cl}$ $cm^{-1}$: 2900, 1760, 1230.

Mass: m/z 200[$M^-$].

The following compounds were produced in the same manner as Example 1(1-1).

(1-2) Ethyl 5-phenyl-1-tetrazoleacetate

Yield: 16.1%.

Feed materials: 5-phenyltetrazole and ethyl bromoacetate.

N.M.R.($CDCl_3$) δ: 1.25(t,3H), 4.26(q,2H), 5.20(s,2H), 7.52–7.68(m,5H).

I.R.$_{84\ Na\ Cl}$ $^{cm-1}$: 2980, 1750, 1220, 1020.

Mass: m/z 232[$M^-$].

(1-3) Isopropyl 5-phenyl-1-tetrazoleacetate

Yield: 16.6%.

Feed materials: 5-phenyltetrazole and isopropyl chloroacetate.

N.M.R.($CDCl_3$) δ: 1.22(d,6H), 5.08(qq,1H), 5.17(s,2H), 7.52–7.69(m,5H).

I.R. $_{\nu Na\ Cl}$ $cm^{-1}$: 2980, 1750, 1220.

Mass: m/z 246[$M^-$].

(1-4) n-Butyl 5-phenyl-1-tetrazoleacetate

Yield: 11.2%.

Feed materials: 5-phenyltetrazole and n-butyl chloroacetate.

N.M.R.($CDCl_3$) δ: 0.90(t,3H), 1.30(qq,2H), 1.57(qq,2H). 4.20(t,2H), 5.2(s,2H), 7.52–7.68(m,5H).

I.R. $_{\nu Na\ Cl}$$cm^{-1}$: 2950, 1750, 1220.

Mass: m/z 260[$M^+$].

(1-5) Methyl 5-(2-methylphenyl)-1-tetrazoleacetate

Yield: 10.4%.

Feed materials: 5-(2-methylphenyl)tetrazole and methyl chloroacetate.

N.M.R.($CDCl_3$) δ: 2.26(s,3H), 3.74(s,3H), 5.03(s,2H). 7.24–7.51 (m,4H).

I.R. $_{\nu Na\ Cl}$ $cm^{-1}$: 2950, 1760, 1220, 990.

Mass: m/z 232[$M^+$].

(1-6) Methyl 5-(3-methylphenyl)-1-tetrazoleacetate.

Yield: 11.4%.

Feed materials: 5-(3-methylphenyl)tetrazole and methyl chloroacetate.

N.M.R.($CDCl_3$) δ: 1.63(s,3H), 3.81(s,3H), 5.20(s,2H), 7.39–7.44(m,4H), 7.49(d,1H).

I.R. $_{\nu Na\ Cl}$ $cm^{-1}$: 2950, 1750, 1220.

Mass: m/z 232[$M^{+1}$.

(1-7) Methyl 5-(4-methylphenyl)-1-tetrazoleacetate

Yield: 10.4%.

Feed materials: 5-(4-methylphenyl)tetrazole and methylchloroacetate.

Melting point: 106°~107° C.

N.M.R.($CDCl_3$) δ: 2.45(s,3H), 3.81(s,3H), 5.20(s,2H), 7.35(d,2H), 7.53(d,2H).

I.R. $_{\nu KB\ r}$ $cm^{-1}$: 3270, 1750, 1610, 1480, 1250, 1220, 990, 830.

Mass: m/z 232[$M^{+1}$9 .

(1-8) Methyl
5-(4-methoxyphenyl)-1-tetrazoleacetate

Yield: 8.5%.

Feed materials: 5-(4-methoxyphenyl)tetrazole and methyl chloroacetate.

N.M.R.($CDCl_3$) δ: 3.82(s,3H), 3.88(s,3H), 5.20(s,2H), 7.05(d,2H), 7.59(d,2H).

I.R. $_{\nu Na\ Cl}$ $cm^{-1}$: 3000, 2950, 1760, 1260, 840.

Mass: m/z 249[$M^+$].

(1-9) Methyl 5-(4-fluorophenyl)-1-tetrazoleacetate

Yield: 10.8%.

Feed materials: 5-(4-fluorophenyl)tetrazole and methyl chloroacaetate.

Melting point: 101°–102.5° C.

N.M.R.($CDCl_3$) δ: 3.82(s,3H), 5.20(s,2H), 7.70(dd,2H), 7.27(dd,2H).

I.R. $_{\nu KB\ r}$ $cm^{-1}$: 2950, 1760, 1480, 1260, 610.

Mass: m/z 236[$M^+$].

(1-10) Ethyl 3-(5-phenyltetrazol-1-yl)propionate

Yield: 15.1%.

Feed materials: 5-phenyltetrazole and ethyl 3-bromopropionate.

N.M.R.($CDCl_3$) δ: 1.23(t,3H), 3.09(t,2H), 4.12(q,2H), 4.67(t,2H), 7.56–7.76(m,5H).

I.R. $_{\nu Na\ Cl}$ $cm^{-1}$: 2980, 1730, 1460, 1200, 1020.

Mass: m/z 246[$M^+$].

(1-11) Ethyl 4-(5-phenyltetrazol-1-yl)butyrate

Yield: 14.2%.

Feed materials: 5-phenyltetrazole and ethyl 4-bromobutyrate.

N.M.R.($CDCl_3$) δ: 1.22(t,3H), 2.28(qq,2H). 2.39(t,2H), 4.08(q,2H), 4.52(t,2H), 7.55–7.72(m,5H).

I.R. $_{\nu Na\ Cl}$ $cm^{-1}$: 2980, 1720, 1470, 1200, 1010, 740.

Mass: m/z 260[$M^+$].

(1-12) Ethyl 5-(5-phenyltetrazol-1-yl)valerate

Yield: 13.2%.

Feed materials: 5-phenyltetrazole and ethyl 5-bromovalerate.

N.M.R.($CDCl_3$) δ: 1.24(t,3H), 1.64(qq,2H), 2.00(qq,2H), 2.31(t,2H), 4.11(q,2H), 4.44(t,2H), 7.56–7.68(m,5H).

I.R. $_{\nu Na\ Cl}$ $cm^{-1}$: 2980, 1730, 1470, 1180, 1030.

Mass: m/z 27.1[$M^-$].

(1-13) Ethyl 2-(5-phenyltetrazol-1-yl)propionate

Yield: 12.2%.

Feed materials: 5-phenyltetrazole and ethyl 2-bromopropionate.

N.M.R.($CDCl_3$) δ: 1.22(t,3H), 1.98(d,3H), 4.22(q,2H), 5.23(q,1H), 7.62–7.72(m,5H).

I.R. $_{\nu Na\ Cl}$ $cm^{-1}$: 2980, 1750, 1470, 1450, 1220, 690.

Mass: m/z 246[$M^+$].

(1-14) Ethyl
2-(5-phenyltetrazol-1-yl)-2-methylpropionate

Yield: 11.7%.

Feed materials: 5-phenyltetrazole and ethyl α-bromoisobutyrate.

N.M.R.($CDCl_3$) δ: 1.20(t,3H), 2.08(s,6H), 4.20(q,2H), 7.63–7.69(m,5H).

I.R. $_{\nu Na\ Cl}$ $cm^{-1}$: 2990, 1750, 1450, 1280, 1020, 740.

Mass: m/z 260[$M^+$].

(1-15) Ethyl 5-(4-hydroxyphenyl)-1-tetrazoleacetate

Yield: 22%.

Feed materials: 5-(4-hydroxyphenyl)tetrazole and ethyl bromoacetate.

N.M.R.($CDCl_3$) δ: 1.27(t,3H,J=7.3 Hz), 4.30(q,2H,J=7.3 Hz), 5.19(s,2H), 7.01(d,2H,J=8.5 Hz), 7.09(bs,1H), 7.52(d, 2H,J=8.5 Hz).

I.R. $_{\nu Na\ Cl}$ $cm^{-1}$: 3190, 1750, 1610, 1480, 1220.

Mass: m/z 277[$M^{30}$ ].

(1-16) Ethyl
5-(4-ethoxycarbonyl-methoxycarbonylphenyl)-1-tetrazoleaetate

Yield: 20%.

Feed materials: 5-(4-carboxyphenyl)tetrazole and ethyl bromoacetate.

N.M.R.($CDCl_3$) δ: 1.27(t,3H,J=7.3 Hz),1.32(t,3H,J= 7.3Hz), 4.27(q,2H,J=7.3 Hz), 4.28(q,2H,J=7.3 Hz), 4.90(s, 2H), 5.22(s,2H), 7.79(dd,2H, J=1.6.6.4 Hz), 8.28(dd,2H,J= 1.6,6.4 Hz).

I.R.$_{\nu Na\ Cl}$ $cm^{-1}$: 3460, 2960, 1720, 1220, 1120, 1020.

Mass: m/z 382[$M^+$].

(1-17) Ethyl
5-(4-piperidinocarbonylphenyl)-1-tetrazoleacetate

Yield: 19%.

Feed materials: 5-(4-piperidinocarbonylphenyl)tetrazole and ethyl bromoacetate.

N.M.R.($CDCl_3$) δ: 1.28(t,3H,J=7.25 Hz), 1.5–1.71(m, 6H), 3.34(bs,2H),3.74(bs,2H), 4.27(q,2H,J=7.25 Hz), 5.18(s,2H), 7.56(dd,2H,J=2.0,6.45 Hz), 7.70(dd,2H,J= 2.0.6.45Hz).

I.R. $_{\nu Na\ Cl}$ $cm^{-1}$: 3470, 2940, 1750, 1630, 1440.

Mass: m/z 342[$M^+$].

(1-18) Ethyl 5-(4-di-n-propylaminocarbonylphenyl)-1-tetrazoleacerate

Yield: 15.4%.

Feed materials: 5-(4-di-n-propylaminocarbonylphenyl)tetrazole, and ethyl bromoacetate.

N.M.R.($CDCl_3$) δ: 0.77(t,3H,J=6.9 Hz), 1.03(t,3H,J=6.9 Hz), 1.28(t,3H,J=6.9 Hz), 1.54–1.73(m,4H), 3.17(t,2H,J= 7.7 Hz), 3.49(t,2H,J=7.7 Hz), 4.27(q,2H,J=6.9 Hz), 5.18(s, 3H), 7.54(d,2H, J=8.1 Hz),7.69(d,2H,J=8.1 Hz).

I.R. $_{\nu Na\ Cl}$ $cm^{-1}$: 3420, 2950, 1750, 1620, 1440.

Mass: m/z 359[$M^+$].

EXAMPLE 2 (REACTION 2)

(2-1 ) Methyl 5-(4-chlorophenyl)-1-tetrazoleacetate

Phosphorus pentachloride (500 mg. 2.88 mM) was slowly added to 13 ml of an anhydrous benzene containing 520 mg of N-(4-chlorobenzoyl)glycine methyl ester (2.29 mM) at room temperature. After stirring at room temperature for 30 min., the reaction mixture was evaporated at 40° C. under reduced pressure. The residue was dissolved in 5 ml of dimethylformamide. The solution was dropwise added to 2 ml of a dimethylformamide suspension containing 300 mg (4.6 mM) of sodium azide at room temperature over 40 to 60 min. while stirring it. After the completion of the addition, the mixture was additionally stirred at room temperature for 30 min. and poured into ice-water. The crystals as precipitated were collected by filtration, washed with water, dried under reduced pressure, and then recrystallized from methanol, to give 230 mg of the object product (yield: 4.0%).

Melting point: 156°~158° C.

N.M.R. ($CDCl_3$) δ: 3.81(s,3H), 5.38(s,2H), 7.96(d,2H), 8.42(d,2H).

I.R.$_{\nu KB\ r}$ $cm^{-1}$: 3100, 2950, 1750, 1520, 1440, 1350, 1220.

Mass: m/z 252[$M^+$].

The following compounds were prepared in the same manner as Example 2 (2-1).

(2-2) Ethyl 5-phenyl-1-tetrazoleacetate

Yield: 41.1%.

Feed material: N-benzoyl glycine ethyl ester.

The analysis data of the compound are the same as those of the compound of Example 1 (1-2).

(2-3) Methyl 5-(4-methylphenyl)-1-tetrazoleacetate

Yield: 50%.

Feed material: N-(4-methylbenzoyl)glycine methyl ester.

The analysis data of the compound are the same as those of the compound of Example 1 (1-7).

(2-4) Methyl 5-(3-nitrophenyl)-1-tetrazoleacetate

Yield: 31%.

Feed material: N-(3-nitrobenzoyl)glycine methyl ester.

Melting point: 122°~123° C.

N.M.R.($CDCl_3$) δ: 3.86(s,3H), 5.53(s,2H), 7.80(t,1H). 8.47(dd,1H), 8.09(d,1H).

I.R.$_{\nu KB\ r}$ $cm^{-1}$: 3000, 1750, 1540, 1520, 1340, 1220, 1000, 820, 710.

Mass: m/z 263[$M^-$].

(2-5) Methyl 5-(4-nitrophenyl)-1-tetrazoleacetate

Yield: 51%.

Feed material: N-(4-nitrobenzoyl)glycine methyl ester.

Melting point: 155°~156° C.

N.M.R.($CDCl_3$) δ: 3.84(s,3H). 5.25(s,2H), 7.90(d,2H), 8.43(d,2H).

I.R.$_{\nu KB\ r}$ $cm^{-1}$: 3100, 2950, 1750, 1520, 1440, 1350, 1220, 980, 850.

Mass: m/z 263[$M^+$].

(2-6) Methyl 5-(3-nitro-4-chlorophenyl)-1-tetrazoleacetate

Yield: 30%.

Feed material: N-(3-nitro-4-chlorobenzoyl)glycine methyl ester.

Melting point: 89°~91° C.

N.M.R.($CDCl_3$) δ: 3.79(s,3H), 5.19(s,2H), 7.71(d,1H), 7.83(d,1H), 8.16(d,1H).

I.R. $_{\nu KB\ r}$ $cm^{-1}$: 3070, 3000, 2950, 1740, 1550, 1340, 1230, 1120.

Mass: m/z 297[$M^+$].

(2-7) Methyl 5-(2-chloro-5-nitrophenyl)-1-tetrazoleacetate

Yield: 39%.

Feed material: N-(2-chloro-5-nitrobenzoyl)glycine methyl ester.

Melting point: 128°~130° C.

N.M.R.($CDCl_3$) δ: 3.75(s,3H), 5.17(s,2H), 7.79(dd,1H), 8.41(dd,1), 8.45(s,1H).

I.R. $_{\nu KB\ r}$ $cm^{-1}$: 3100, 3070, 3000, 2950, 1750, 1620, 1520, 1350, 1220.

Mass: m/z 297[$M^+$].

(2-8) Butyl 3'-(1-ethoxycarbonylmethyl-tetrazol-5-yl)oxanilate

Yield: 46.3%.

Feed material: N-[3-(butoxyoxamido)benzoyl]glycine ethyl ester.

Melting point: 103°~105° C.

N.M.R.($CDCl_3$) δ: 0.99(t,3H), 1.27(t,3H), 1.45(qq,2H), 1.80(qq,2H), 4.30(q,2H), 4.37(t,2H), 5.27(s,2H), 7.56(d, 2H), 7.71–7.74(m,1H), 8.13(d,1H), 9.05(bs, 1H).

I.R. $_{\nu KB\ r}$ $cm^{-1}$: 3100, 2950, 1740, 1700, 1600, 1280, 1220, 800.

Mass: m/z 375[$M^+$].

(2-9) Methyl 5-(3-nitro-4-methylphenyl)-1-tetrazoleacetate

Yield: 51%.

Feed material: N-(3-nitro-4-methylbenzoyl)glycine methyl ester.

Melting point: 85°~86° C.

N.M.1. ($CDCl_3$) δ: 2.72(s,3H), 5.25(s,2H), 7.70(d,1H), 7.88(dd,1H), 8.29(d,1H).

I.R. $_{KB\ r}$ $cm^1$: 3000, 2950, 1750, 1520, 1340, 1230.

Mass: m/z 252[$M^+$].

(2-10)
1,4-Bis(1-methoxycarbonylmethyl-tetrazol-5-yl)benzene

Yield: 40%.

Feed material N,N'-bis(methoxycarbonylmethyl-)terephthalamide.

Melting point: 182°~183° C.,

N.M.R.(DMSO-$d_6$) δ: 3.68(s,6H), 5.73(s,4H), 8.0(s,4H).

I.R. $_{\nu KB\ r}$ $cm^{-1}$: 3080, 3000, 2950, 1750, 1730, 1440, 1220.

Mass: m/z 358[$M^+$].

(2-11) Methyl 5-(4-ethylphenyl)-1-tetrazoleacetate

Yield: 36%.

Feed material: N-(4-ethylbenzoyl)glycine methyl ester.

N.M.R.($CDCl_3$) δ: 1.29(t,3H), 2.74(dd,2H). 3.81(s,3H), 5.20(s,2H), 7.37(d,2H), 7.56(d,2H).

I.R. $_{\nu Na\ Cl}$ $cm^{-1}$: 2950, 1750, 1620, 1480, 1440, 1220, 840.

Mass: m/z 246[$M^{+1}$].

(2-12) Methyl
5-(4-n-butylphenyl)-1-tetrazoleacetate

Yield: 55%.

Feed material: N-(4-n-butylbenzoyl)glycine methyl ester.

N.M.R.($CDCl_3$) δ: 0.94(t,3H), 1.39(qq,2H), 1.64(qq,2H), 2.70(t,2H), 3.81(s,3H), 5.20(s,2H), 7.45(d,2H), 7.55(d,2H).

I.R. $_{\nu Na\ Cl}$ $cm^{-1}$: 2900, 1750, 1610, 1480, 1460, 1220.

Mass: m/z 272[$M^+$].

(2-13) Methyl 5-(3-fluorophenyl)-1-tetrazoleacetate

Yield: 40%.

Feed material: N-(3-fluorobenzoyl)glycine methyl ester.

N.M.R.(CDCl3) δ: 3.83(s,3H), 5.22(s,2H), 7.28–7.60(m, 4H).

I.R. $_{\nu Na\ Cl}$ $cm^{-1}$: 2950, 1760, 1590, 1480, 1230, 880, 800.

Mass: m/z 236[$M^+$].

(2-14) Methyl 5-(2-chlorophenyl)-1-terazoleacetate

Yield: 45%.

Feed material: N-(2-chlorobenzoyl)glycine methyl ester.

N.M.R.($CDCl_3$) δ: 3.71(s,3H), 5.13(s,2H), 7.27–7.59(m, 4H).

I.R. $_{\nu Na\ Cl}$ $cm^{-1}$: 3600, 2950, 1760, 1460, 1220, 990, 800.

Mass: m/z 252[$M^+$].

(2-15) Methyl
5-(3,4-dimethylphenyl)-1-tetrazoleacetate

Yield: 50%.

Feed material: N-(3,4-dimethylbenzoyl)glycine methyl ester.

N.M.R.($CDCl_3$) δ: 2.33(s,6H), 5.20(s,2H), 7.30–7.31(m, 2H), 7.45(s, 1H).

I.R. $_{\nu Na\ Cl}$ $cm^{-1}$: 2950, 1750, 1480, 1440, 1360, 1220, 990, 790.

Mass: m/z 246[$M^+$].

(2-16) Methyl 5-(4-biphenylyl)-1-tetrazoleacetate

Yield: 46.4%.

Feed material: N-(4-biphenyloyl)glycine methyl ester.

Melting point: 146°~147° C.

N.M.R.($CDCl_3$) δ: 3.84(s,3H), 5.26(s,2H), 7.36–7.80(m, 9H).

I.R. $_{\nu KB\ r}$ $cm^{-1}$: 2910, 1760, 1730, 1470, 1210.

Mass: m/z 294[$M^-$].

(2-17) Methyl
5-(4-n-heptylphenyl)-1-tetrazoleacetate

Yield: 51%.

Feed material: N-(4-n-heptylbenzoyl)glycine methyl ester.

Melting point: 54°~55° C.

N.M.R.($CDCl_3$) δ: 0.88(t,3H), 1.28–1.36(m,8H), 1.64(m, 2H), 2.69(t,2H), 3.82(s,3H), 5.20(s,2H), 7.35(d,2H), 7.55(d, 2H).

I.R. $_{\nu KB\ r}$ $cm^{-1}$: 2910, 2850, 1740, 1440, 1370, 1260, 1220.

Mass: m/z 316[$M^+$].

(2-18) Methyl
5-(4-phenoxyphenyl)-1-tetrazoleacetate

Yield: 46%.

Feed material: N-(4-phenoxybenzoyl)glycine methyl ester.

N.M.R.($CDCl_3$) δ: 3.82(s,3H), 5.20(s,2H), 7.10–7.25(m, 5H), 7.42(t,2H), 7.62(d,2H).

I.R. $_{\nu Na\ Cl}$ $cm^{-1}$: 3000, 2950. 1750, 1610, 1580, 1470, 1440, 1360, 1240, 750.

Mass: m/z 310[$M^+$].

(2-19) Methyl 5-(4-t-butylphenyl)-1-tetrazoleacetate

Yield: 51%.

Feed material: N-(4-t-butylbenzoyl)glycine methyl ester.

N.M.R.($CDCl_3$) δ: 1.37(s,9H), 3.83(s,3H), 5.21(s,2H), 7.58(s,4H).

I.R. $_{\nu Na\ Cl}$ $cm^{-1}$: 2950, 1750, 1610, 1480, 1440, 1360, 1260, 1220, 1110, 1000, 840.

Mass: m/z 274[$M^+$].

(2-20) Methyl 5-(4-n-butoxyphenyl)-1
-tetrazoleacetate

Yield: 46%.

Feed material: N-(4-n-butoxybenzoyl)glycine methyl ester.

N.M.R.($CDCl_3$) δ: 0.99(t,3H), 1.47–1.61 (m,2H), 3.82(s, 3H), 4.03(t,2H), 5.19(s,2H), 7.03(d,2H), 7.58(d,2H).

I.R. $_{\nu Na\ Cl}$ $cm^{-1}$: 2950, 1760, 1610, 1480, 1250, 1220, 840.

Mass: m/z 290[$M^+$].

(2-21 ) Methyl 5-(2-biphenylyl)-1-tetrazoleacetate

Yield: 38%.

Feed material: N-(2-biphenyloyl)glycine methyl ester.

N.M.R.($CDCl_3$) δ: 3.55(s,3H), 4.37(s,2H), 7.13–7.70(m, 9H).

I.R. $_{\nu Na\ Cl}$ $cm^{-1}$: 3000, 2950, 1760, 1430, 1220, 980.

Mass: m/z 294[$M^+$].

(2-22) Methyl
5-(3,5-dimethylphenyl)-1-tetrazoleacetate

Yield: 60%.

Feed material: N-(3,5-dimethylbenzoyl)glycine methyl ester.

N.M.R.($CDCl_3$) δ: 2.39(s,6H), 3.82(s,3H), 5.20(s,2H), 7.23(s,1H), 7.27(s,2H).

I.R. $_{\nu Na\ Cl}$ $cm^{-1}$: 2960, 1760, 1470, 1440, 1240, 1220.

Mass: m/z 246[$M^+$].

(2-23) Methyl
5-(3-trifluoromethylphenyl)-1-tetrazoleacetate

Yield: 61%.

Feed material: N-(3-trifluoromethylbenzoyl)glycine methyl ester.

Melting point: 75°~76° C.

N.M.R.($CDCl_3$) δ: 3.84(s,3H), 5.22(s,2H), 7.70–7.96(m, 4H).

I.R. $_{\nu KB\ r}$ $cm^{-1}$: 2970, 1750, 1440, 1340, 1230, 1120.

Mass: m/z 286[$M^-$].

(2-24) Methyl
5-(4-n-heptoxyphenyl)-1-tetrazoleacetate

Yield: 57.3%.

Feed material: N-(4-n-heptoxybenzoyl) glycine methyl ester.

Melting point: 51°~52° C.

N.M.R.($CDCl_3$) δ: 0.90(t,3H,J=6.45 Hz). 1.32–1.46(m, 2H), 1.80(m,2H), 3.82(s,3H), 4.03(t,4H,J=6.45 Hz), 5.19(s, 2H, 7.03(d,2H,J=8.86 Hz), 7.58(d,2H,J=8.86 Hz).

I.R. $_{\nu KB\ r}$ $cm^{-1}$: 2950, 2850, 1760, 1620, 1260.

Mass: 332[$M^+$].

(2-25) Methyl
5-(3-methoxyphenyl)-1-tetrazoleacetate

Yield: 42.8%.

Feed material: N-(3-methoxybenzoyl)glycine methyl ester.

N.M.R.($CDCl_3$) δ: 3.82(s,3H), 3.86(s,3H), 5.21(s,2H), 7.10–7.22(m,3H), 7.43–7.49(m,1H).

I.R. $_{\nu Na\ Cl}$ $cm^{-1}$: 3000, 2950, 1750, 1580, 1480, 1440, 1280, 1230, 1220, 1030.

Mass: m/z 249[$M^+$].

(2-26) Methyl
5-(3,4-dimethoxyphenyl)-1-tetrazoleacetate

Yield: 63.7%.

Feed material: N-(3,4-dimethoxybenzoyl)glycine methyl ester.

Melting point: 129.5°~130.5° C.

N.M.R.($CDCl_3$) δ: 3.82(s,3H), 3.93(s,3H), 3.96(s,3H), 5.21(s,2H), 6.99(d,1H,J=8.48 Hz), 7.15(dd,1H,J=2.02, 8.46 Hz), 7.27(d,1H,J=2.02 Hz).

I.R. $_{\nu KB\ r}$ $cm^{-1}$: 3000, 2950, 1750, 1610, 1500, 1440, 1240, 1020.

Mass: m/z 278[$M^+$].

(2-27) Methyl
5-(3,4-di-n-butoxyphenyl)-1-tetrazoleacetate

Yield: 74.5%.

Feed material: N-(3,4-di-n-butoxybenzoyl)glycine methyl ester.

Melting point: 77°~78° C.

N.M.R.($CDCl_3$) δ: 0.99(t,3H,J=7.25 Hz), 1.00(t,3H,J=7.25 Hz), 1.48–1.55(m,6H), 1.79–1.85(m,4H), 3.82(s,3H), 4.03(dd,2H,J=6.45, 10.48 Hz), 5.20(s,2H), 6.97(d,1H,J=8.46 Hz), 7.10(dd,1H,J=2.02,8.46 Hz), 7.24(d,1H,J=2.02 Hz).

I.R. $_{84\ KB\ r}$ $cm^{-1}$: 2950, 1760, 1600, 1500, 1440, 1220.

Mass: m/z 362[$M^+$].

(2-28) Methyl
5-(3,4,5-trimethoxyphenyl)-1-tetrazoleacetate

Yield: 73.5%.

Feed material: N-(3,4,5-trimethoxybenzoyl)glycine methyl ester.

Melting point: 99.5°~100.5° C.

N.M.R.($CDCl_3$) δ: 3.84(s,3H), 3.89(s,6H), 3.92(s,3H), 5.21(s,2H), 6.88(s,2H).

I.R. $_{\nu KB\ r}$ $cm^{-1}$: 2950, 1740, 1590, 1500, 1440, 1240, 1120, 1000.

Mass: m/z 308[$M^+$].

(2-29) Methyl
5-(4-bromomethylphenyl)-1-tetrazoleacetate

Yield: 41%.

Feed material: N-(4-bromomethylbenzoyl)glycine methyl ester.

N.M.R.($CDCl_3$) δ: 3.82(s,3H),4.66(s,2H), 5.20(s,2H), 7.58(d,2H, J=8.5 Hz), 7.67(d,2H, J=8.5 Hz).

I.R. $_{\nu Na\ Cl}$ $cm^{-1}$: 3000, 2950, 1750, 1440, 1220, 990.

Mass: m/z 311[$M^+$].

(2-30) Methyl
5-(4-methylthiophenyl)-1-tetrazoleacetate

Yield: 44%.

Feed material: N-(4-methyithiobenzoyl)glycine methyl ester.

N.M.R.($CDCl_3$) δ: 2.54(s,3H), 3.82(s,3H), 5.20(s,2H), 7.37(d,2H,J=8.5 Hz), 7.57(d,2H, J=8.5 Hz).

I.R. $_{\nu Na\ Cl}$ $cm^{-1}$: 3000, 2950, 1750, 1600, 1440, 1220.

Mass: m/z 264 [$M^+$].

(2-31) Methyl
5-(4-n-butylaminosulfonylphenyl)-1-tetrazoleacetate

Yield: 38%.

Feed material: N-(4-n-butylaminosulfonylbenzoyl)glycine methyl ester.

N.M.R.($CDCl_3$) δ: 0.88(t,3H,J=7.2 Hz), 1.23–1.39(m, 2H), 1.44–1.54(m,2H), 3.00–3.06(m,2H), 3.84(s,3H), 4.55(t,1H,J=6.0 Hz), 5.23(s,2H), 7.83(dd,2H,J=1.6,8.5 Hz), 8.05(dd,2H,J=1.6,8.5 Hz).

I.R. $\nu_{Na\ Cl}$ $cm^{-1}$: 3280, 2960, 1760, 1440, 1330.

Mass: m/z 353[$M^+$].

(2-32) Methyl 5-(4-diisopropylaminosulfonylphenyl)-1-tetrazoleacetate

Yield: 46%.

Feed material: N-(4-diisopropylaminosulfonylbenzyoyl)glycine methyl ester.

Melting point: 140°~141° C.

N.M.R.($CDCl_3$) δ: 1.28(s,6H), 1.31(s,6H), 3.77(q,1H,J=6.65 Hz) 3.83(s,3H), 5.21(s,2H), 7.79(dd,2H,J=1.6, 6.85 Hz), 8.05(dd,2H,J=l.6, 6.85 Hz).

I.R. $\nu_{KB\ r}$ $cm^{-1}$: 3420, 1750, 1330, 1150.

Mass: m/z 356[$M^+$].

(2-33) Methyl 5-(3,5-di-t-butyl-4-hydroxyphenyl)-1-tetrazoleacetate

Yield: 40%.

Feed material: N-(3.5-di-t-butyl-4-hydroxybenzoyl)glycine methyl ester.

Melting point: 135°~137° C.

N.M.R.($CDCl_3$) δ: 1.46(s,18H), 3.84(s,3H), 5.18(s,2H), 5.64(s,1H), 7.45(s,2H).

I.R. $\nu_{KB\ r}$ $cm^{-1}$: 3600, 2950, 1750, 1420, 1220, 1100.

Mass: m/z 346[$M^+$].

(2-34) Methyl 5-(3,5-di-t-butyl-4-methoxyphenyl)-1-tetrazoleacetate

Yield: 40%.

Feed material: N-(3,5-di-t-butyl-4-methoxybenzoyl)glycine methyl ester.

Melting point: 110°~111° C.

N.M.R.($CDCl_3$) δ: 1.44(s,18H), 3.74(s,3H), 3.84(s,3H), 5.18(s,2H), 7.52(s,2H).

I.R. $\nu_{KB\ r}$ $cm^{-1}$: 2950, 1750, 1400, 1220, 1000.

Mass: m/z 360[$M^+$].

EXAMPLE 3 (REACTION 3)

(3-1) 5-Phenyl-1-tetrazoleacetic acid

A mixture of 100 mg of methyl 5phenyl-1-tetrazoleacetate, 0.6 ml of acetic acid and 1 ml of a 4N-hydrochloric acid was stirred at 80° to 90° C. for 2 hours. The reaction solution was evaporated under reduced pressure. The precipitated solid was filtered, washed with cold water and recrystallized from 50% ethanol-water, to give 64.1 mg (yield: 69.2%) of 5-phenyhetrazole-lacetic acid.

Melting point: 179°~180° C. (decomposition).

N.M.R.(DMSO-$d_6$) δ: 3.42(bs,3H). 5.51(s,2H), 7.59–7.78(m,5H).

I.R. $\nu_{KB\ r}$ $cm^{-1}$: 3000, 2500, 1730, 1460, 1230.

Mass: m/z 204[$M^+$].

The following compounds were obtained in the same manner as Example 3 (3-1).

(3-2) 5-(3-Nitro-4-chlorophenyl)-1-tetrazoleacetic acid

Yield: 41%.

Melting point: 189° to 190° C. (decoposition)

Feed material: methyl 5-(3-nitro-4-chlorophenyl)-1-tetrazolacetate.

N.M.R.(DMSO-$d_6$) δ: 3.35(bs,4H), 5.59(s,3H), 8.01(d, 2H), 8.48(d,1H).

I.R.$\nu_{KB\ r}$ $cm^{-1}$: 3080, 3050, 2950, 1720, 1530, 1440, 1360, 1210.

Mass: m/z 283[$M^+$].

(3-3) 5-(4-Fluorophenyl)-1-tetrazoleacetic acid

Yield: 50%.

Feed material: methyl 5-(4-fluorophenyl)-1-tetrazoleacetate.

Melting point: 159°~160° C. (decomposition).

N.M.R.(DMSO-$d_6$) δ: 3.34(bs,3H), 5.5(s,2H), 7.34(dd, 2H), 7.84(dd,2H).

I.R. $\nu_{KB\ r}$ $cm^{-1}$: 3000, 2570, 1760, 1740, 1610, 1480, 1240, 840.

Mass: m/z 222[$M^+$].

(3-4) 5-(2-Methylphenyl)-1-tetrazoleacetic acid

Yield: 58.7%.

Feed material: methyl 5-(2-methylphenyl)-1-tetrazoleacetate.

Melting point: 142°~143° C. (decomposition).

N.M.R.(DMSO-$d_6$) δ: 2.18(s,3H), 3.43(bs,3H), 5.25(s, 2H), 7.35–7.55(m,4H).

I.R. $\nu_{KB\ r}$ $cm^{-1}$: 3000, 2500, 1750, 1420, 1220, 1100, 820.

Mass: m/z 218[$M^+$].

(3-5) 5-(3-Methylphenyl)-1-tetrazoleacetic acid

Yield: 61.2%.

Feed material: methyl 5-(3-methylphenyl)-1-tetrazoleacetate.

Melting point: 140°~141.5° C. (decomposition).

N.M.R.(DMSO-$d_6$) δ: 2.40(s,2H), 3.42(bs,3H), 5.50(s, 2H), 7.44–7.58(m,4H).

I.R. $\nu_{KB\ r}$ $cm^{-1}$: 2920, 1730, 1220, 1210, 800.

Mass: m/z 218[$M^+$].

(3-6) 5-(4-Methylphenyl)-1-tetrazoleacetic acid

Yield: 80%.

Feed material: methyl 5-(4-methylphenyl)-1-tetrazoleacetate.

Melting point: 171°~172° C.

N.M.R.(DMSO-$d_6$) δ: 2.40(s,3H), 3.44(bs,3H), 5.49(s, 2H), 7.42(d,2H), 7.64(d,2H).

I.R. $\nu_{KB\ r}$ $cm^{-1}$: 3000, 2550, 1760, 1740, 1610, 1480, 1230, 820, 740.

Mass: m/z 218[$M^+$].

(3-7) 5-(4-Methoxyphenyl)-1-tetrazoleacetic acid

Yield: 58.7%.

Feed material: methyl 5-(4-methoxyphenyl)-1-tetrazoleacetate.

Melting point: 139°~140° C. (decomposition).

N.M.R.(DMSO-$d_6$) δ: 3.56(bs,3H), 3.85(s,3H), 5.48(s, 2H), 7.15(d,2H), 7.70(d,2H).

I.R. $_{\nu KB\ r}$ $cm^{-1}$: 3550, 3420, 2510, 1730, 1610, 1480, 1270, 840.

Mass: m/z 234[$M^+$].

(3-8) 5-(3-Nitrophenyl)-1-tetrazoleacetic acid

Yield: 70%.

Feed material: methyl 5-(3-nitrophenyl)-1-tetrazoleacetate.

Melting point: 215°~219° C. (decomposition).

N.M.R.(DMSO-$d_6$) δ: 3.35(bs,5H), 5.58(s,2H), 7.93(t, 1H), 8.20(d,1H), 8.49(dd,1H), 8.56(s,1H),

I.R. $_{\nu KB\ r}$ $cm^{-1}$: 2960, 1740, 1530, 1350, 1220.

Mass: m/z 249[$M^+$].

(3-9) 5-(4-Nitrophenyl)-1-tetrazoleacetic acid

Yield: 70.4.%.

Feed material: methyl 5-(4-nitrophenyl)-1-tetrazoleacetate.

Melting point: 226°~227° C. (decomposition).

N.M.R.(DMSO-$d_6$) δ: 3.40(bs, 1H), 5.60(s,2H), 8.07(d, 2H), 8.43(d,2H).

I.R. $_{KB\ r}$ $cm^{-1}$: 3100, 2970, 1730, 1600, 1520, 1440, 1330, 1230, 1000, 860.

Mass: m/z 249[$M^+$].

(3-10) 5-(4-Chlorophenyl)-1-tetrazoleacetic acid

Yield: 50%.

Feed material: methyl 5-(4.-chlorophenyl)-1-tetrazoleacetate.

Melting point: 225°~226° C. (decomposition).

N.M.R.(DMSO-$d_6$) δ: 3.34(bs,3H), 5.60(s,2H), 8.06(d, 2H), 8.44(d,2H).

I.R. $_{\nu KB\ r}$ $cm^{-1}$: 3100, 2950, 1740, 1520, 1440, 1340, 1240, 860.

Mass: m/z 238[$M^+$].

(3-11) 5-(3-Nitro-4-methylphenyl)-1-tetrazoleacetic acid

Yield: 68.5%.

Feed material: methyl 5-(3-nitro4-methylphenyl)-1-tetrazoleacetate.

Melting point: 199°~200° C. (decomposition).

N.M.R.(DMSO-$d_6$) δ: 2.61(s,3H), 3.30(bs,3H), 5.58(s, 2H), 7.50(d,1H), 8.00(dd,1H), 8.35(d,1H).

I.R. $_{\nu KB\ r}$ $cm^{-1}$: 3050, 2970, 1730, 1530, 1210.

Mass: m/z 263[$M^+$].

(3-12) 3'-(1-Carboxymethyl-tetrazol-5-yl)oxanilic acid

Yield: 66%.

Feed material: butyl 3'-(1-ethoxycarbonylmethyl-tetrazol-5-yl) oxanilate.

Melting point: 220°~221° C. (decomposition).

N.M.R.(DMSO-$d_6$) δ: 3.17(s,2H), 5.49(s,2H), 7.28–7.55(m,4H).

I.R. $_{\nu KB\ r}$ $cm^{-1}$: 2900, 2600, 1740, 1240.

Mass: m/z 259[$M^+$].

(3-13)

1,4-Bis(1-carboxymethyl-tetrazol-5-yl)benzene

Yield: 72.3%.

Feed material: 1,4-bis(methoxycarbonylmethyl-tetrazole-5-yl) benzene.

Melting point: 263°~264° C. (decomposition).

N.M.R.(DMSO-$d_6$) δ: 3.54(bs, 10H), 5.59(s,4H, 8.01 (s,4H).

I.R. $_{\nu KB\ r}$ $cm^{-1}$: 3000, 2950, 2570, 1760, 1730, 1460, 1230, 800.

Mass: m/z 300[$M^+$].

(3-14) 5-(4-n-Butylphenyl)-1-tetrazoleacetic acid

Yield: 52%.

Feed material: methyl 5-(4-n-butylphenyl)-1-tetrazoleacetate.

Melting point: 119°~120° C.

N.M.R.(DMSO-$d_6$) δ: 0.91(t,3H), 1.35(qq,2H), 1.59(qq, 2H), 2.67(t,2H), 2.50(bs,3H), 5.50(s,2H), 7.43(d,2H), 7.67(d,2H).

I.R. $_{\nu KB\ r}$ $cm^{-1}$: 3000, 2950, 2920, 1730, 1240.

Mass: m/z 260[$M^+$].

(3-15) 3-(5-Phenyltetrazol-1-yl)propionic acid

Yield: 70.4%.

Feed material: ethyl 3-(5-phenyltetrazol-1-yl)propionate.

Melting point: 116°~118° C. (decomposition).

N.M.R.(DMSO-$d_6$) δ: 2.99(t,2H), 3.38(bs,1H), 4.62(t, 2H), 7.64–7.83(m,5H).

I.R. $_{\nu KB\ r}$ $cm^{-1}$: 2900, 1720, 1310, 1200, 700.

Mass: m/z 218[$M^+$].

(3-16) 4-(5-Phenyltetrazol-1-yl)buatyric acid

Yield: 68.1%.

Feed material: ethyl 4-(5-phenyltetrazol-1-yl)butyrate.

Melting point: 131°~132° C. (decomposition).

N.M.R.(DMSO-$d_6$) δ: 2.04(qq,2H), 2.30(t,2H), 3.34(bs, 3H), 4.52(t,2H), 7.62–7.8(m,5H).

I.R. $_{\nu KB\ r}$ $cm^{-1}$: 2950, 1730, 1460, 1200, 780.

Mass: m/z 232[$M^+$].

(3-17) 5-(5-Phenyltetrazol-1-yl)valeric acid

Yield: 65.5%.

Feed material: ethyl 5-(5-phenyltetrazol-1-yl)valerate.

Melting point: 105°~106° C. (decomposition).

N.M.R.(DMSO-$d_6$) δ: 1.44(qq,2H), 1.83(qq,2H), 2.19(t, 2H), 3.34(bs,3H), 4.49(t,2H), 7.64–7.67(m,5H).

I.R. vKB $rcm^{-1}$: 2950, 1720, 1460, 1210, 740.

Mass: m/z 246[$M^+$].

(3-18) 2-(5-Phenyltetrazol-1-yl)propionic acid

Yield: 64.1%.

Feed material: ethyl 2-(5-phenyltetrazol-1-yl)propionate.

Melting point: 187°~188° C. (decomposition).

N.M.R.(DMSO-d $_6$) δ: 1.83(d,3H), 3.35(bs,3H), 5.55(q, 1H), 7.62–7.72(m,5H).

I.R. $_{\nu KB\ r}$ $cm^{-1}$: 2900, 2550, 1740, 1460, 1240, 1180, 740.

Mass: m/z 218[$M^+$].

(3-19) 2-(5-Phenyltetrazol-1-yl)-2-methylpropionic acid

Yield: 66.9%

Feed material: ethyl 2-(5-phenyltetrazol-1-yl)- 2-methylpropionate.

Melting point: 184°~185° C. (decomposition).

N.M.R.(DMSO-$d_6$) δ:2.79(s,6H), 3.34(bs,3H), 7.63–7.78(m,5H).

I.R. $_{\nu KB\ r}$ $cm^{-1}$:2950, 1740, 1450, 1190, 990, 730, 680.

Mass: m/z 232[$M^{30}$ ].

(3-20) 5-(3-Fluorophenyl)-1-tetrazoleacetic acid

Yield: 60%.

Feed material: ethyl 5(3-fluorophenyl)-1-tetrazoleacetate.

Melting point: 134°~135° C. (decomposition).

N.M.R.(DMSO-$d_6$) δ: 3.33(bs,3H), 5.56(s,2H), 7.49–7.72(m,4H).

I.R. $_{\nu KB\ r}$ $cm^{-1}$: 3000, 2910, 2590, 1740, 1480, 1240, 880.

Mass: m/z 222[$M^+$].

(3-21 ) 5-(2-Chlorophenyl)-1-tetrazoleacetic acid

Yield: 58%.

Feed material: methyl 5-(2-chlorophenyl)-1-tetrazoleacetate.

Melting point: 155°~157° C. (decomposition).

N.M.R.(DMSO-$d_6$) δ: 3.34(bs,3H), 5.30(s,2H), 7.58(d, 1H), 7.64–7.75(m,2H).

I.R. $_{\nu KB\ r}$ $cm^{-1}$: 3000, 2960, 2520, 1730, 1600, 1440, 1220, 810, 750.

Mass: m/z 238[$M^+$].

(3-22) 5-(3,4-Dimethylphenyl)-1-tetrazoleacetic acid

Yield: 60%.

Feed material: methyl 5-(3,4-dimethylphenyl)-1-tetrazoleacetate.

Melting point: 225°~226° C. (decomposition).

N.M.R.(DMSO-$d_6$) δ: 2.30(s,6H), 5.49(s,2H), 7.36(d, 1H), 7.47(d,1H), 7.54(s,1H).

I.R. $_{\nu KB\ r}$ $cm^{-1}$: 2920, 1730, 1460, 1220, 840.

Mass: m/z 232[$M^+$].

(3-23) 5-(4-Biphenylyl)-1-tetrazoleacetic acid

Yield: 76.8%.

Feed material: methyl 5-(4-biphenyly)-1-tetrazoleacelate.

Melting point: 183°~184° C. (decomposition).

N.M.R.(DMSO-$d_6$) δ: 3.35(bs,2H), 5.51(s,2H), 7.41–7.94(m,9H).

I.R. $_{\nu KB\ r}$ $cm^{-1}$: 3420, 2930, 1740, 1480, 1220.

Mass: m/z 280[$M^-$].

(3-24) 5-(4-n-Heptylphenyl)-1-tetrazoleacetic acid

Yield: 81%.

Feed material: methyl 5-(4-n-heptylphenyl)-1-tetrazoleacetate.

Melting point: 127°~129° C. (decomposition).

N.M.R.($CDCl_3$) δ: 0.89(t,3H), 1.25–1.34(m,8H), 1.62–1.68(m, 2H), 2.69(t,2H), 5.15(s,2H), 7.35(d,2H), 7.60(d,2H).

I.R. $_{\nu KB\ r}$ $cm^{-1}$: 2910, 2850, 1760, 1740, 1240.

Mass: m/z 302[$M^+$].

(3-25) 5-(4-Phenoxyphenyl)-1-tetrazoteacetic acid

Yield: 69%.

Feed material: methyl 5-(4-phenoxyphenyl)-1-tetrazoleacetate.

Melting point: 161°~161.5° C. (decomposition).

N.M.R.(DMSO-$d_6$) δ: 5.16(s,2H), 7.10–7.45(m,7H), 7.66(d,2H).

I.R.$_{\nu KB\ r}$ $cm^{-}$: 3000, 2950, 1760, 1730, 1580, 1470, 1240.

Mass: m/z 296[$M^+$].

(3-26) 5-(4-t-Butylphenyl)-1-tetrazoleacetic acid

Yield: 55%.

Feed material: methyl 5-(4-t-Butylphenyl)-1-tetrazoleacetate.

Melting point: 186°~187° C. (decomposition).

N.M.R.(DMSO-$d_6$) δ: 1.33(s,9H), 5.50(s,2H), 7.66(q, 4H).

I.R. $_{\nu KB\ r}$ $cm^{-1}$: 2950, 1740, 1730, 1480, 1430, 1220, 840.

Mass: m/z 260[$M^+$].

(3-27) 5-(4-n-Butoxyphenyl)-1-tetrazoleacetic acid

Yield: 63%.

Feed material: methyl 5-(4-n-butoxyphenyl)-1-tetrazoleacetate.

Melting point: 135°~136° C. (decomposition).

N.M.R.(DMSO-$d_6$) δ: 0.95(t,3H), 1.45(q,2H), 1.72(q, 2H), 4.06(t,2H), 5.45(s,2H), 7.13(d,2H), 7.68(d,2H).

I.R. $_{\nu KB\ r}$ $cm^{-1}$: 2920, 1760, 1730, 1620, 1480, 1250.

Mass: m/z 276[$M^+$].

(3-28) 5-(2-Biphenylyl)-1-tetrazoleacetic acid

Yield: 50%.

Feed material: methyl 5-(2-Biphenylyl)-1-tetrazoleacetate.

N.M.R.(DMSO-$d_6$) δ: 4.36(s,2H), 7.06–7.64(m,9H), 7.84(bs,2H).

I.R. $_{\nu Na\ Cl}$ $cm^{-1}$: 3000, 2950, 1740, 1430, 1250.

Mass: m/z 280[$M^+$].

(3-29) 5-(3,5-Dimethylphenyl)-1-tetrazoleacetic acid

Yield: 76%.

Feed material: methyl 5-(3,5-dimethylphenyl)-1-tetrazoleacetate.

Melting point: 187°~188° C. (decomposition).

N.M.R.(DMSO-$d_6$) δ: 2.35(s,6H), 3.33(bs,2H), 5.49(s, 2H), 7.27(s, 1H), 7.35(s,2H).

I.R. $_{\nu KB\ r}$ $cm^{-1}$: 2920, 1730, 1220, 860.

Mass: m/z 232[$M^+$].

(3-30) 5-(3-Trifluoromethylphenyl)-1-tetrazoleacetic acid

Yield: 67%.

Feed material: methyl 5-(3-trifluoromethylphenyl)-1-tetrazoleactate.

Melting point: 169°~170° C. (decomposition).

N.M.R. (DMSO-$d_6$) δ:3.35(bs,2H), 5.60(s,2H), 7.88–8.11(m,4H).

I.R. $_{\nu KB\ r}$ $cm^{-1}$: 3000, 1740, 1450, 1330, 1240, 1120.

Mass: m/z 272[$M^+$].

(3-31) 5-(4-Hydroxyphenyl)-1-tetrazoleacetic acid

Yield: 82%.

Feed material: ethyl 5-(4-hydroxyphenyl)-1-tetrazoleacetate.

Melting point: 220°~222° C. (decomposition).

N.M.R. (DMSO-$d_6$) δ:5.16(s,2H), 4.7–6.4.(bs,1H), 7.00(dd,2H, J=2.6,9.2 Hz), 7.52(dd,2H,J=2.6,9.2 Hz), 9.70(bs,1H).

I.R. $_{\nu KB\ r}$ $cm^{-1}$: 3140, 1730, 1600, 1470, 1280.

Mass: m/z 220[$M^-$].

(3-32) 5-(4-n-Heptoxyphenyl)-1-tetrazoleacetic acid

Yield: 70%.

Feed material: methyl 5-(4-n-heptoxyphenyl)-1-tetrazoleacetate.

Melting point: 131°~132° C. (decomposition).

N.M.R. ($CDCl_3$+DMSO-$d_6$) δ:0.90(t,3H,J=6.44 Hz), 1.33–1.48(m, 8H), 1.80(m,2H), 4.02(t,2H, J=6.60 Hz), 5.13(s,2H), 7.02(d,2H, J=8.87 Hz), 7.63(d,2H,J=8.46 Hz).

I.R. $_{\nu KB\ r}$ $cm^{-1}$: 3000, 2900, 1730, 1610, 1480, 1250, 1230, 740.

Mass: m/z 318[$M^-$].

(3-33) 5-(3-Methoxyphenyl)-1-tetrazoteacetic acid

Yield: 71.9%.

Feed material: methyl 5-(3-methoxyphenyl)-1-tetrazoleacetate.

Melting point: 179.5°~180.5° C. (decomposition).

N.M.R.(DMSO-$d_6$) δ:3.86(s,3H), 5.21(s,2H), 7.12–7.44(m,3H), 7.47–7.55(m, 1H).

I.R. $_{\nu KB\ r}$ $cm^{-1}$: 3000, 2500, 1730, 1600, 1540, 1490, 1240, 1120, 1020, 800.

Mass: m/z 234.[$M^+$].

(3-34) 5-(3,4-Dimethoxyphenyl)-1-tetrazoleacetic acid

Yield: 72.4%.

Feed material: methyl 5-(3,4-dimethoxyphenyl)-1-tetrazoleacetate.

Melting point: 193.5°~194.5° C. (decomposition).

N.M.R. ($CDCl_3$+DMSO-$d_6$) δ:3.92(s,3H), 3.96(s,3H). 5.17(s,2H), 7.01(d,1H,J=8.46 Hz), 7.22(dd, 1H,J=2.01,8.46 Hz). 7.28(d,1H, J=2.42 Hz).

I.R.$_{\nu KB\ r}$ $cm^{-1}$: 3000, 1730, 1610, 1500, 1460, 1220, 1020, 820.

Mass: m/z 264[$M^+$].

(3-35) 5-(3,4-Di-n-butoxyphenyl)-1-tetrazoleacetic acid

Yield: 71.1%.

Feed material: methyl 5-(3,4-di-n-butoxyphenyl)-1-tetrazoleacetate.

Melting point: 141°~142° C. (decomposition).

N.M.R.(DMSO-$d_6$) δ: 0.99(t,3H,J=7.0 Hz), 1.00(t,3H,J=7.0 Hz), 1.45–1.60(m,4H), 1.76–1.89(m,4H), 4.01–4.10(m, 4H), 6.98–7.38(m,4H).

I.R.$_{\nu KB\ r}$ $cm^{-1}$: 3420, 2950, 1730, 1610, 1500, 1460, 1210, 1140, 810.

Mass: m/z 348[$M^+$].

(3-36) 5-(3,4,5-Trimethoxyphenyl)-1-tetrazoleacetic acid

Yield: 87%.

Feed material: methyl 5-(3,4,5-trimethoxyphenyl)-1-tetrazoleacetate.

Melting point: 234°~235° C. (decomposition).

N.M.R.($CDCl_3$+DMSO-$D_6$) δ: 3.89(s,3), 3.92(s,3H), 5.18(s,2H), 6.94(s,2H).

I.R.$_{\nu KB\ r}$ $cm^{-1}$: 3000, 2950, 1730, 1590, 1490, 1420, 1220, 1120, 1000.

Mass: m/z 294[$M^+$].

(3-37) 5-(4-Carboxyphenyl)-1-tetrazoleacetic acid

Yield: 85%.

Feed material: ethyl 5-(4-ethoxycarbonylmethoxycarbonylphenyl)-1-tetrazoleacetate.

Melting point: 271°~273° C. (decomposition).

N.M.R.(DMSO-$d_6$) δ: 2.7–4.8(br,1H), 5.44(s,2H), 7.36(d, 2H, J=8.4 Hz), 8.16(d,2H,J=8.4 Hz), 12.2–13.7(br,1H).

I.R.$_{\nu KB\ r}$ $cm^{-1}$: 3420, 1740, 1690, 1420, 1290, 1240.

Mass: m/z 248[$M^+$].

(3-38) 5-(4-Piperidinocarbonylphenyl)-1-tetrazoleacetic acid

Yield: 88%.

Feed material: ethyl 5-(4-piperidinocarbonylphenyl)-1-tetrazoleacetate.

Melting point: 226°~227° C. (decomposition).

N.M.R.(DMSO-$d_6$) δ: 1.56(bs,2H), 1.71(bs,2H), 3.36(bs, 2H), 3.72(bs,2H), 3.2–5.0(br. 1H), 5.23(s,2H), 7.57(d,2H,J=8.4 Hz), 7.77(d,2H,J=8.4 Hz).

I.R.$_{\nu KB\ r}$ $cm^{-1}$: 3430, 2930, 1740, 1570, 1450.

Mass: m/z 314[$M^+$].

(3-39) 5-(4-Di-n-propylaminocarbonylphenyl)-1-tetrazoleacetic acid

Yield: 88%.

Feed material: ethyl 5-(4-di-n-propylaminocarbonylphenyl)- 1-tetrazoleacetate.

Melting point: 188°~189° C. (decomposition).

N.M.R.(DMSO-$d_6$) δ: 0.77(t,3H,J=7.3 Hz), 1.00(t,3H,J=7.3 Hz), 1.56(q,t,2H,J=7.3,7.7 Hz), 1.71(q,t,2H, J=7.8,7.7 Hz), 3.18(t,2H,J=7.7 Hz), 3.47(t,2H,J=7.7 Hz), 3.73(br, 1H), 5.22(s,2H), 7.53(d,2H,J=8.3 Hz), 7.76(d,2H,J=8.3 Hz).

I.R. $_{\nu KB\ r}$ $cm^{-1}$: 3400, 2900, 1730, 1560, 1220.

Mass: m/z 331[$M^+$].

(3-40) 5-(4-Aminophenyl)-1-tetrazoleacetic acid

Yield: 42.6%.

Feed material: methyl 5-(4-aminophenyl)-1-tetrazoleacetate.

Melting point: 183° C. (decomposition).

N.M.R.(DMSO-$d_6$) δ: 5.03(s,2H), 6.66(d,2H,J=8.46 Hz), 7.45(d,2H,J=8.86 Hz).

I.R. $_{\nu KB\ r}$ $cm^{-1}$: 3420, 1760, 1620, 1480, 1370, 830.

Mass: m/z 219[$M^{-1}$].

(3-41) 5-(4-Bromomethylphenyl)-1-tetrazoleacetic acid

Yield: 75%.

Feed material: methyl 5-(4-bromomethylphenyl)-1-tetrazoleacetate.

Melting point: 171°~173°C. (decomposition).

N.M.R.(DMSO-$d_6$) δ: 4.56(s,2H), 5.48(s,2H), 7.54(d,2H, J=8.46 Hz), 7.74(d,2H,J=8.46 Hz).

I.R. $_{\nu KB\ r\ cm}{}^{-1}$: 3200, 2980, 1760, 1420, 1220.

Mass: m/z 297[$M^+$].

(3-42) 5-(4-Methylthiophenyl)-1-tetrazoleacetic acid

Yield: 80%.

Feed material: methyl 5-(4-methylthiophenyl)-1-tetrazoleacetate.

Melting point: 160°~163° C. (decomposition).

N.M.R.(DMSO-$d_6$) δ: 2.55(s,2H), 3.44(bs,3H), 5.49(s, 2H), 7.46(d,2H,J=8.46 Hz), 7.69(d,2H,J=8.46 Hz).

I.R. $_{\nu KB\ r}$ $cm^{-1}$: 3400, 2900, 1740, 1600, 1200.

Mass: m/z 250[$M^+$].

(3-43) 5-(4-Methylsulfinylphenyl)-1-tetrazoleacetic acid

Yield: 74%.

Feed material: methyl 5-(4-methylsulfinylphenyl)-1-tetrazoleacetate.

Melting point: 238°~240° C. (decomposition).

N.M.R.(DMSO-$d_6$) δ: 2.82(s,3H) 5.43(s,2H, 7.91(d,2H, J=8.46 Hz), 7.93(d,2H,J=8.46 Hz).

I.R. $_{\nu KB\ r}$ $cm^{-1}$: 3420, 2500, 1760, 1460, 1230, 1000.

Mass: m/z 301[$M^+$].

(3-44) 5-(4-Methylsulfonylphenyl)-1-tetrazoleacetic acid

Yield: 72%.

Feed material: methyl 5-(4-methylsulfonytphenyl)-1-tetrazoleacetate.

Melting point: 214°~216° C. (decomposition).

N.M.R.(DMSO-$d_6$) δ: 3.19(s,3H), 5.34(s,2H), 8.00(d,2H, J=8.46 Hz), 8.15(d,2H,J=8.46 Hz).

I.R. $_{\nu KB\ r}$ $cm^{-1}$: 3000, 1730, 1300, 1240, 1150.

Mass: m/z 317 [$M^+$].

(3-45)
5-(4-n-Butylaminosulfonylphenyl)-1-tetrazoleacetic acid

Yield: 78%.

Feed material: methyl 5-(4-n-butylaminosulfonylphenyl)-1-tetrazoleacetate.

Melting point: 148°~149° C. (decomposition).

N.M.R.(DMSO-$d_6$) δ: 0.87(t,3H,J=7.3 Hz), 1.25–1.53(m, 4H), 2.89–2.94(m,2H), 3.20–4.30(br,1H), 5.23(s,2H), 7.11(t,1H,J=5.1 Hz), 7.86(d,1H, J=8.7 Hz), 8.05(d,1H,J=8.7 Hz).

I.R. $_{\nu KB\ r}$ $cm^{-1}$: 3560, 3270, 2950, 1740, 1440, 1320, 1240, 1160, 1090.

Mass: m/z 339[$M^+$].

(3-46)
5-(4-Diisopropylaminosulfonylphenyl)-1-tetrazoleacetic acid

Yield: 87%.

Feed material: methyl 5-(4-diisopropylaminosulfonylphenyl)- 1-tetrazoleacetate.

Melting point: 215°~216° C. (decomposition).

N.M.R.(DMSO-$d_6$) δ: 1.28(s,6H), 1.30(s,6H), 3.77(q,1H, J=6.6 Hz), 3.7–4.2(br,1H), 5.26(s,2H), 7.88(d,2H,J=7.7 Hz), 8.03(d,2H,J=7.7 Hz).

I.R.$_{\nu KB\ r}$ $cm^{-1}$: 3420, 2970, 1740, 1440, 1320.

Mass: m/z 367[$M^+$].

(3-47)
5-(3,5-Di-t-butyl-4-hydroxyphenyl)-1-tetrazoleacetic acid

Yield: 62%.

Feed material: methyl 5-(3,5-di-t-butyl-4-hydroxyphenyl)- 1-tetrazoleacetate.

Melting point: 118°~119° C. (decomposition).

N.M.R.(DMSO-$d_6$) δ: 1.40(s,18H), 3.36(bs,1H), 5.09(s, 2H), 7.53 (s,2H), 7.63(s,1H).

I.R. $_{\nu KB\ r}$ $cm^{-1}$: 3440, 2950, 1610, 1420, 1380, 1240,

Mass: m/z 332[$M^+$].

(3-48)
5-(3,5-Di-t-butyl-4-methoxyphenyl)-1-tetrazoleacetic acid

Yield: 78%.

Feed material: methyl 5-(3,5-di-t-butyl-4-methoxyphenyl)- 1-tetrazoleacetate.

Melting point: 164°~165° C. (decomposition).

N.M.R. (DMSO-$d_6$) δ: 1.41(s,18H), 3.35(bs,1H), 3.71(s, 3H), 5.38 (s,2H), 7.60(s,2H).

I.R.$_{\nu KB\ r}$ $cm^{-1}$: 3440, 2950, 1740, 1450, 1410, 1230.

Mass: m/z 346[$M^+$].

EXAMPLE 4 (REACTION 4)

(4-1) 5-(3-n-Butyloxalylaminophenyl)tetrazole 5-(3-Aminophenyl)tetrazole (1.7 g) was added to 12 ml of n-butyloxalate and reacted at a bath temperature of 165° to 175° C. for 1.5 hr while stirring. After cooling, the precipitated crystals were filtered off and recrystallized from acetone-n-hexane, to give 2.3 g (yield: 75%) of 5-(3-n-butyloxalylaminophenyl)tetrazole.

Melting point: 157°~158° C. (J.P. Kokoku No. 59-1705).

The following compounds were obtained in the same manner as Example 4 (4-1). These compounds are known. In the parentheses after the melting points, the publications showing the manufacturing process are listed.

(4-2) 5-(2-n-Butyloxalylaminophenyl)tetrazole

Melting point: 132°~137° C. (J.P. Kokoku No. 59-1704).

(4-3)
5-(4-Chloro-3,5-diethyloxalylaminophenyl)tetrazole

Melting point: 214°~215.5° C. (decomposition) (J.P. Kokoku No. 59-1704).

(4-4)
5-(4-Chloro-3,5-di-n-butyloxalylaminophenyl)tetrazole

Melting point: 217°~218° C. (J.P. Kokoku No. 59-1707).

(4-5) 5-(3-Ethyloxalylaminophenyl)tetrazole

Melting point: 193°~195° C. (J.P. Kokoku No. 59-1705).

EXAMPLE 5 (REACTION 5)

(5-1 ) 3-(1H-Tetrazol-5-yl)oxanilic acid

Five grams of the compound obtained from Example 4 (4-5), namely 5-(3-ethyloxalylaminophenyl)tetrazole or ethyl 3-(1H-tetrazol-5-yl) oxanilate, were dissolved in 35 ml of ethanol. Sodium hydroxide solution (0.5N, 100 ml) was dropwise added to the solution, while cooling them with water. After the addition, the temperature was gradually raised and the reaction was conducted at room temperature for 3 hr. The resultant solution was dropwise added to 70 ml of4N hydrochloric acid at room temperature. After the addition, the mixture was stirred for 1 hr and then the precipitated crystals were filtered. The crystals were washed with water, to give 3.9 g of 3-(1H-tetrazol-5-yl)oxanilic acid (yield: 87.4%).

The crystals were further recrystallized from isopropyl alcohol-water.

Melting point: 241°~243° C. (decomposition) (J.P. Kokai No. 63-4570).

TABLE 4

| Compound | $R_1$ | $R_2$ | $R_3$ | $R_4$ |
|---|---|---|---|---|
| 1-1 | $-CH_2COOCH_3$ | H | H | H |
| 2 | $-CH_2COOC_2H_5$ | " | " | " |
| 3 | $-CH_2COO_1-C_3H_7$ | " | " | " |
| 4 | $-CH_2COOn\text{-}Bu$ | " | " | " |
| 5 | $-CH_2COOCH_3$ | $2\text{-}CH_3$ | " | " |
| 6 | " | $3\text{-}CH_3$ | " | " |
| 7 | " | $4\text{-}CH_3$ | " | " |
| 8 | " | $4\text{-}OCH_3$ | " | " |
| 9 | " | 4-F | " | " |
| 10 | $-CH_2CH_2COOC_2H_5$ | H | " | " |
| 11 | $-CH_2(CH_2)_2COOC_2H_5$ | " | " | " |
| 12 | $-CH_2(CH_2)_3COOC_2H_5$ | " | " | " |
| 13 | $-CH(CH_3)-COOC_2H_5$ | " | " | " |
| 14 | $-C(CH_3)_2COOC_2H_5$ | " | " | " |
| 15 | $-CH_2COOC_2H_5$ | 4-OH | " | " |
| 16 | " | $4\text{-}CO_2CH_2CO_2C_2H_5$ | " | " |
| 17 | " | 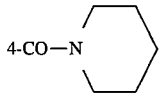 | " | " |
| 18 | " | $4\text{-}CO-N(n\text{-}C_3H_7)_2$ | " | " |
| 2-1 | $-CH_2COOCH_3$ | 4-Cl | H | H |
| 2 | $-CH_2COOC_2H_5$ | | | |
| 3 | $-CH_2COOCH_3$ | $4\text{-}CH_3$ | " | " |
| 4 | " | $3\text{-}NO_2$ | " | " |
| 5 | " | $4\text{-}NO_2$ | " | " |
| 6 | " | $3\text{-}NO_2$ | 4-Cl | " |
| 7 | " | 2-Cl | $5\text{-}NO_2$ | " |
| 8 | $-CH_2COOC_2H_5$ | 3-NHCOCOOn-Bu | H | " |
| 9 | $-CH_2COOCH_3$ | $3\text{-}NO_2$ | $4\text{-}CH_3$ | " |
| 10 | " | 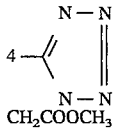 | H | " |
| 11 | " | $4\text{-}C_2H_5$ | " | " |

TABLE 4-continued

| Compound | $R_1$ | $R_2$ | $R_3$ | $R_4$ |
|---|---|---|---|---|
| 12 | " | 4-n-Bu | " | " |
| 13 | " | 3-F | " | " |
| 14 | " | 2-Cl | " | " |
| 15 | " | 3-$CH_3$ | 4-$CH_3$ | " |
| 16 | " | 4-Ph | H | " |
| 17 | " | 4-n-$C_7H_{15}$ | " | " |
| 18 | " | 4-O−Ph | " | " |
| 19 | " | 5-t-Bu | " | " |
| 20 | " | 4-O-n-Bu | " | " |
| 21 | " | 2-Ph | " | " |
| 2-22 | −$CH_2COOCH_3$ | 3-$CH_3$ | 5-$CH_3$ | H |
| 23 | " | 3-$CF_3$ | H | " |
| 24 | " | 4-O-n-$C_7H_{15}$ | " | " |
| 25 | " | 3-$OCH_3$ | " | " |
| 26 | " | 3-$OCH_3$ | 4-$OCH_3$ | " |
| 27 | " | 3-O-n-Bu | 4-O-n-Bu | " |
| 28 | " | 3-$OCH_3$ | 4-$OCH_3$ | 5-$OCH_3$ |
| 29 | " | 4-$CH_2Br$ | H | H |
| 30 | " | 4-S−$CH_3$ | " | " |
| 31 | " | 4-$SO_2$−NH-n-Bu | " | " |
| 32 | " | 4-$SO_2$−N−(i-$C_3H_7$)$_2$ | " | " |
| 33 | " | 3-t-Bu | 4-OH | 5-t-Bu |
| 34 | " | 3-t-Bu | 4-$OCH_3$ | " |
| 3-1 | −$CH_2COOH$ | H | H | H |
| 2 | " | 3-$NO_2$ | 4-Cl | " |
| 3 | " | 4-F | H | " |
| 4 | " | 2-$CH_3$ | " | " |
| 5 | " | 3-$CH_3$ | " | " |
| 6 | " | 4-$CH_3$ | " | " |
| 7 | " | 4-$OCH_3$ | " | " |
| 8 | " | 3-$NO_2$ | " | " |
| 9 | " | 4-$NO_2$ | " | " |
| 3-10 | −$CH_2COOH$ | 4-Cl | H | H |
| 11 | " | 3-$NO_2$ | 4-$CH_3$ | " |
| 12 | " | 3-NHCOCOOH | H | " |
| 13 | " | 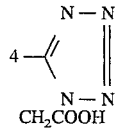 | " | " |
| 14 | " | 4-n-Bu | " | " |
| 15 | −$CH_2CH_2COOH$ | H | " | " |
| 16 | −$CH_2(CH_2)_2COOH$ | " | " | " |
| 17 | −$CH_2(CH_2)_3COOH$ | " | " | " |
| 18 | −$CH(CH_3)COOH$ | " | " | " |
| 19 | −$C(CH_3)_2COOH$ | " | " | " |
| 20 | −$CH_2COOH$ | 3-F | " | " |
| 21 | " | 2-Cl | " | " |
| 22 | " | 3-$CH_3$ | 4-$CH_3$ | " |
| 23 | " | 4-Ph | H | " |
| 24 | " | 4-n-$C_7H_{15}$ | " | " |
| 25 | " | 4-O−Ph | " | " |
| 26 | " | 4-t-Bu | " | " |
| 27 | " | 4-O-n-Bu | " | " |
| 28 | " | 2-Ph | " | " |
| 29 | " | 3-$CH_3$ | 5-$CH_3$ | " |
| 30 | " | 3-$CF_3$ | H | " |
| 3-31 | −$CH_2COOH$ | 4-OH | H | H |
| 32 | " | 4-O-n-$C_7H_{15}$ | " | " |
| 33 | " | 3-$OCH_3$ | " | " |
| 34 | " | 3-$OCH_3$ | 4-$OCH_3$ | " |
| 35 | " | 3-O-n-Bu | 4-O-n-Bu | H |
| 36 | " | 3-$OCH_3$ | 4-$OCH_3$ | 5-$OCH_3$ |
| 37 | " | 4-COOH | H | H |
| 38 | " | 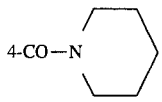 | " | " |
| 39 | " | 4-CON(n-$C_3H_7$)$_2$ | " | " |
| 40 | " | 4-$NH_2$ | " | " |
| 41 | " | 4-$CH_2Br$ | " | " |
| 42 | " | 4-$SCH_3$ | " | " |

TABLE 4-continued

| Compound | $R_1$ | $R_2$ | $R_3$ | $R_4$ |
|---|---|---|---|---|
| 43 | " | 4-SO−$CH_3$ | " | " |
| 44 | " | 4-$SO_2$−$CH_3$ | " | " |
| 45 | " | 4-$SO_2$−NH-n-Bu | " | " |
| 46 | " | 4-$SO_2$−N(i-$C_3H_7$)$_2$ | " | " |
| 47 | " | 3-t-Bu | 4-OH | 5-t-Bu |
| 48 | " | " | 4-$OCH_3$ | " |
| 4-1 | H | 3-NHCOCOOn-Bu | H | H |
| 2 | " | 2-NHCOCOOn-Bu | " | " |
| 3 | " | 3-NHCOCOOC$_2$H$_5$ | 4-Cl | 5-NHCOCOOC$_2$H$_5$ |
| 4 | H | 3-NHCOCOOn-Bu | 4-Cl | 5-NHCOCOOn-Bu |
| 5 | " | 3-NHCOCOOC$_2$H$_5$ | H | H |
| 5-1 | H | 3-NHCOCOOH | H | H |

*Bu = Butyl group
*Ph = Phenyl group

EXPERIMENT 1

Aldose Reductase Inhibition Test (1) Test Procedure

Six-week-old male SD rats were killed under ether anesthesia and their crystalline lenses were immediately removed and stored at −80° C. The lenses were homogenized in 3 volumes of 135 mM sodium potassium phosphate buffer (pH: 7.0) and centrifuged at a rate of 30,000 rpm for 30 min. The supernatant was dialyzed overnight against 0.05M sodium chloride, to produce an aldose reductase solution. All operations were conducted at 4° C. The enzyme solution was stored at −80° C.

The activity of aldose reductase was determined according to a slight modification of the method of J. H. Kinoshita et al [J. Biol. Chem., 240, 877 (1965)]. Namely, 0.1 ml of DL-glycerine aldehyde (final concentration: 10 mM) was added to 0.9 ml of 100 mM sodium potassium phosphate buffer (pH 6.2) which contained lithium sulfate (final concentration: 400 mM), reduced nicotinamide adenine dinucleotide phosphate (final concentration: 0.15 mM), the enzyme solution, and the compound to be tested (final concentration: $5\times10^{-5}$M or $10^{-6}$M), and then the reaction was conducted at 30° C. for 5 min. During this reaction, the absorbance at 340 nm was observed with the lapse of time. The maximum reducing rate of the absorbance (U) during the reaction was determined. By substracting, from this value, the maximum reducing rate ($U_o$) at 340 nm of the reaction solution before the addition of the substrate (DL-glycerine aldehyde), the reaction rate (V) ($V=U-U_o$) was calculated as a true reaction rate in the presence of the compound to be tested.

The same procedure was repeated except for the absence of the compound to be tested. A true reaction rate ($V_o$) in case the enzyme was not inhibited was calculated ($V_o=U'-U_o'$). The inhibitory activity of aldose reductase was determined by the following formula.

$$\text{Inhibition (\%)} = \frac{V_0 - V}{V_0} \times 100$$

(2) Results

The results of Experiment 1 are shown in table 5.

The results show that the present compounds provide excellent aldose reductase inhibitory activity at a concentration of $5\times10^{5}$M or $1\times10^{-6}$M.

TABLE 5

| Compound to be tested | Inhibition (%) |
|---|---|
| 1-1 | 92 |
| 4 | 63 |
| 6 | 44 |
| 7 | 59 |
| 8 | 43 |
| 2-1 | 31 |
| 4 | 30 |
| 5 | 44 |
| 6 | 42 |
| 8 | 52 |
| 10 | 36 |
| 3-1 | 97* |
| 2 | 84* |
| 3 | 94* |
| 5 | 96* |
| 6 | 98* |
| 7 | 95* |
| 10 | 85* |
| 11 | 92* |
| 12 | 97* |
| 13 | 94* |
| 15 | 80 |
| 16 | 79 |
| 17 | 68 |
| 18 | 91 |
| 23 | 95* |
| 24 | 96* |
| 3-25 | 94* |
| 26 | 94* |
| 27 | 96* |
| 4-1 | 58 |
| 2 | 69 |
| 3 | 95 |
| 4 | 92 |
| 5-1 | 63 |

*Concentration of $10^{-6}$M

EXPERIMENT 2

(1) Test Procedure

In the same manner as Experiment 1, the inhibitions at final concentrations of $10^{-6}$, $10^{-7}$ and $10^{8}$M for the compound to be tested were calculated. Based on these values, a concentration for inhibiting the aldose reductase activity by 50% ($IC_{50}$ (M)) was calculated. As a control, the same experiment was conducted for the known aldose reductase inhibitor, ONO-2235[(E)-3-carboxymethyl- 5-[(2E)-methyl-3-phenylpropenylidene]rhodanine].

(2) Results

The results are shown in Table 6 below. It is apparent that the present compounds provide aldose reductase inhibitory activity which are equivalent or superior to that of the known aldose reductase inhibitor (ONO-2235).

TABLE 6

| Compound to be tested | $IC_{50}$ $(10^{-8})M$ |
|---|---|
| 3-1 | 3.2 |
| 3-3 | 4.2 |
| 3-5 | 3.3 |
| 3-6 | 2.5 |
| 3-7 | 4.8 |
| 3-11 | 4.2 |
| 3-12 | 3.1 |
| 3-13 | 2.7 |
| 3-14 | 1.7 |
| 3-23 | 2.2 |
| 3-24 | 1.7 |
| 3-25 | 2.8 |
| 3-26 | 2.7 |
| 3-27 | 1.8 |
| 3-31 | 4.3 |
| 3-32 | 2.9 |
| 3-33 | 2.8 |
| 3-34 | 6.3 |
| 3-35 | 3.3 |
| 3-37 | 8.2 |
| 3-38 | 5.4 |
| 3-39 | 7.3 |
| 3-40 | 4.1 |
| 3-41 | 2.0 |
| 3-42 | 3.7 |
| 3-45 | 7.8 |
| ONO-2235 (Control) | 2.2 |

EXPERIMENT 3 (ACUTE TOXICITY TEST)

(1) Test Procedure

The compound listed in Table 7 and suspended in 0.5% sodium carboxymethyl cellulose was orally administered to male MCH mice (6 weeks old: 5 animals per test group).

The symptom of these test animals was observed for 14 days after the administration and $LD_{50}$ was estimated from the number of animals died during this term. During the test, the mice were able to take food and water freely.

(2) Results

The results are shown in Table 7. $LD_{50}$ for each of the compounds is above 3,000 mg/kg.

TABLE 7

| Compound to be tested (Example No.) | $LD_{50}$ (mg/kg) |
|---|---|
| 1-7 | >3000 |
| 3-1 | >3000 |
| 3-6 | >3000 |
| 3-12 | >3000 |

What is claimed is:

1. A compound having the following formula (I):

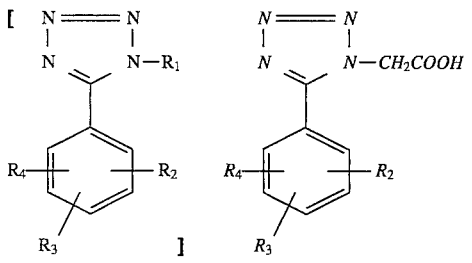

(I)

[wherein $R_1$ is —A—$COOR_5$, and where A is an alkylene group having 1 to 4 carbon atoms and $R_5$ is a hydrogen atom or a lower alkyl group; and]

*wherein*

$R_2$, $R_3$, and $R_4$ are selected from the group consisting of a hydrogen atom, a hydroxy group, a halogen group, a carboxyl group, an alkyl group, an amide group, an amino group, an alkoxy group, an aryl group, an aryloxy group, an alkylthio group, an alkylsulfinyl group, an alkylsulfonyl group, a nitro group, —NH-$COCOOR_6$ where $R_6$ is a hydrogen atom or lower alkyl group, a mono- or dialkylaminosulfonyl group, and a residual group having the following formula (II):

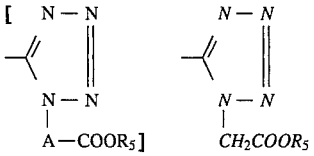

(II)

[and where A and $R_5$ are the same as above;

with the proviso that the compound of formula (I) does not include the following combination of substituents:

wherein A is an ethylidene group or isopropylidene group, $R_5$ is a hydrogen atom or ethyl group, and $R_2$, R3, and $R_4$ are hydrogen atoms;

wherein A is a methylene group, $R_5$ is a hydrogen atom, a methyl group or an ethyl group, and $R_2$, $R_3$ and $R_4$ are hydrogen atoms;

wherein A is a trimethylene group or tetramethylene group, $R_5$ is a hydrogen atom or a methyl group, and $R_2$, $R_3$ and $R_4$ are hydrogen atoms; and wherein A is a methylene group, $R_5$ is a hydrogen atom or an ethyl group, $R_2$ and $R_3$ are hydrogen atoms, and $R_4$ is a 3- or 4-bromine atom, a 3- or 4-chlorine atom, a 3- or 4-nitro group, a 3- or 4-methyl group or a 3-trifluoromethyl group] *with the proviso that $R_2$, $R_3$, and $R_4$ are not all hydrogen atoms, and with the further proviso that when $R_2$ and $R_3$ are hydrogen atoms, $R_4$ is not a 3- or 4-bromine atom, a 3- or 4- chlorine atom, a 3- or 4-nitro group, a 3- or 4-methyl group or a 3-trifluoromethyl group.*

[2. A composition comprising an effective amount of a compound in combination with a physiologically acceptable additive, said compound having the following formula (I):

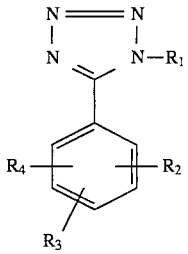

(I)

wherein $R_1$ is —A—$COOR_3$, and where A is an alkylene group having 1 to 4 carbon atoms and $R_5$ is a hydrogen atom or a lower alkyl group; and $R_2$, $R_3$ and $R_4$ are selected from the group consisting of a hydrogen atom, a hydroxy group, a halogen atom, a carboxyl group, an alkyl group, an amide group, an amino group, an alkoxy group, an aryl group, an aryloxy group, an alkylthio group, an alkylsulfinyl group, an alkylsulfonyl group, a nitro group, —NH- $COCOOR_6$ where R6 is a hydrogen atom or a lower alkyl group, a mono-or dialkylaminosulfonyl group, and a residual group having the following formula (II):

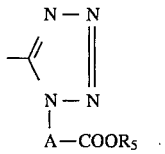

(II)

and where A and $R_5$ are the same as above:

with the proviso that the compound of formula (I) does not include the following combination of substituents:

wherein A is an ethylidene group or isopropylidene group, $R_5$is a hydrogen atom or an ethyl group, and $R_2$, $R_3$ and $R_4$ are hydrogen atoms;

wherein A is a methylene group, $R_5$ is a hydrogen atom, a methyl group or an ethyl group, $R_2$, $R_3$ and $R_4$ are hydrogen atoms;

wherein A is a trimethylene group or a tetramethylene group, $R_5$ is a hydrogen atom or a methyl group, and $R_2$, $R_3$ and $R_4$ are hydrogen atoms; and wherein A is a methylene group, $R_5$ is a hydrogen atom or an ethyl group, $R_2$ and $R_3$ are hydrogen atoms, and $R_4$ is a 3- or 4-bromine atom, a 3- or 4-chlorine atom, a 3-or 4-nitro group, a 3-or 4-methyl group or a 3-trifluoromethyl group.]

3. A method for alleviating diabetic complications in an animal comprising administering to the animal an effective amount of a compound having the following formula (I):

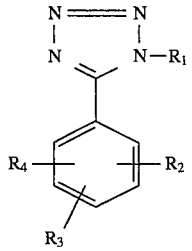

(I)

wherein $R_1$ is a hydrogen atom or —A—$COOR_5$, and where A is an alkylene group having 1 to 4 carbon atoms and $R_5$ is a hydrogen atom or a lower alkyl group; and $R_2$, $R_3$ and $R_4$ are selected from the group consisting of a hydrogen atom, a hydroxy group, a halogen atom, a carboxyl group, an alkyl group, an amide group, an amino group, an alkoxy group, an aryl group, an aryloxy group, an alkylthio group, an alkylsulfinyl group, an alkylsulfonyl group, a nitro group, —NH-$COCOOR_6$ where $R_6$ is a hydrogen atom or a lower alkyl group, a mono-or dialkylaminosulfonyl group, and a residual group having the following formula (II):

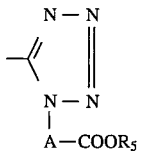

(II)

and where A and $R_5$ are the same as above.

4. The method of claim 3 wherein the compound is administered to the animal in an amount ranging from 1 to 1000 mg per adult animal.

5. The method of claim 4 wherein the administration is made by oral administration, intravenous injection, subcutaneous injection, intramuscular injection or local medication.

6. The method of claim 3 wherein the compound is admixed with a physiologically acceptable additive prior to administration.

7. A method of inhibiting aldose reductase in an animal comprising administering to the animal an effective amount of a compound having the following formula (I):

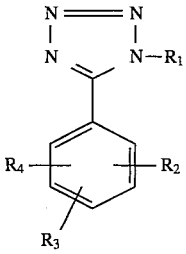

(I)

wherein $R_1$ is a hydrogen atom or —A—$COOR_5$, and where A is an alkylene group having 1 to 4 carbon atoms and $R_5$ is a hydrogen atom or a lower alkyl group; and $R_2$, $R_3$ and $R_4$ are selected from the group consisting of a hydrogen atom, a hydroxy group, a halogen atom, a carboxyl group, an alkyl group, an amide group, an amino group, an alkoxy group, an aryl group, an arytoxy group, an alkylthio group, an alkylsulfinyl group, an alkylsulfonyl group, a nitro group —NHCO-$COOR_6$, where $R_6$, is a hydrogen atom or a lower alkyl group, a mono- or dialkylaminosulfonyl group, and a residual group having the following formula (II):

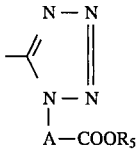

(II)

and where A and $R_5$ are the same as above.

8. The method of claim 7 wherein said compound is administered to the animal in an amount ranging from 1 to 1000 mg per adult animal.

9. The method of claim 7 wherein the administration is made by oral administration, intravenous injection, subcutaneous injection, intramuscular injection or local medication.

10. The method of claim 7 wherein the compound is admixed with a physiologically acceptable additive prior to administration.

*11. A composition comprising an effective amount of a compound of claim 1 in combination with a physiologically acceptable additive.*

* * * * *

UNITED STATES PATENT AND TRADEMARK OFFICE

CERTIFICATE OF CORRECTION

PATENT NO. : Re. 35,281
DATED : June 18, 1996
INVENTOR(S) : Sinji Inukai, Mitsuzi Agata, Kiyoshi Akiba, Takeo Ohmura, Yoshihiro Horio, Yasuhiro Ootake, Shohei Sawaki and Masayoshi Goto.

It is certified that error appears in the above-indentified patent and that said Letters Patent is hereby corrected as shown below:

In column 34, claim 1, line 20, in the second structure, please delete "$CH_2COOR_5$" and insert therefor--$CH_2COOH$--.

In column 34, claim 2, line 59, please delete "—A—$COOR_3$" and insert therefor——A—$COOR_5$--.

In column 35, claim 2, line 1, please delete "R6" and insert therefor--$R_6$--.

In column 36, claim 7, line 35, please delete "arytoxy" and insert therefor--aryloxy--.

In column 36, claim 7, line 37, following "$R_6$", please delete ",".

Signed and Sealed this
First Day of October, 1996

Bruce Lehman

*Attest:*

BRUCE LEHMAN

*Attesting Officer*

*Commissioner of Patents and Trademarks*